United States Patent
Ajima

(10) Patent No.: US 9,867,569 B2
(45) Date of Patent: Jan. 16, 2018

(54) METHOD, APPARATUS, AND SYSTEM FOR ESTIMATING BODY FAT

(71) Applicant: KYOCERA CORPORATION, Kyoto (JP)

(72) Inventor: Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 303 days.

(21) Appl. No.: 14/389,659

(22) PCT Filed: Jun. 19, 2014

(86) PCT No.: PCT/JP2014/003305
§ 371 (c)(1),
(2) Date: Sep. 30, 2014

(87) PCT Pub. No.: WO2014/203539
PCT Pub. Date: Dec. 24, 2014

(65) Prior Publication Data
US 2016/0242695 A1     Aug. 25, 2016

(30) Foreign Application Priority Data

Jun. 19, 2013 (JP) .................................. 2013-128266
Aug. 30, 2013 (JP) .................................. 2013-180320
(Continued)

(51) Int. Cl.
*A61B 5/00*     (2006.01)
*A61B 5/107*    (2006.01)
(Continued)

(52) U.S. Cl.
CPC ............ *A61B 5/4872* (2013.01); *A61B 5/067* (2013.01); *A61B 5/107* (2013.01); *A61B 5/1072* (2013.01);
(Continued)

(58) Field of Classification Search
CPC .................................................. A61B 5/4872
See application file for complete search history.

(56) References Cited

U.S. PATENT DOCUMENTS 8,095,211 B2  1/2012  Tamura et al.
8,527,040 B2  9/2013  Murakawa et al.
(Continued)

FOREIGN PATENT DOCUMENTS

CN    102772225 A    11/2012
EP    2 522 278 A1   11/2012
(Continued)

OTHER PUBLICATIONS

International Search Report; PCT/JP2014/003305; dated Aug. 19, 2014.
(Continued)

*Primary Examiner* — Michael C Stout
*Assistant Examiner* — Nicholas E Kolderman
(74) *Attorney, Agent, or Firm* — Studebaker & Brackett PC

(57) ABSTRACT

A method, an apparatus, and a system for estimating body fat that are capable of measuring a portion of an abdominal outline by a simple method are provided.
A method of estimating the body fat according to the present embodiments includes: a step of obtaining orientation information and motion information of the apparatus itself; a step of calculating a portion of an abdominal outline by a control unit based on the orientation information and the motion information; and a step of estimating, based on the portion of the abdominal outline, at least one of a visceral fat area and a subcutaneous fat area of the abdominal cross-section.

18 Claims, 23 Drawing Sheets

(30) Foreign Application Priority Data

Nov. 28, 2013 (JP) .............................. 2013-246574
Jan. 29, 2014 (WO) ................. PCT/JP2014/000460

(51) Int. Cl.

| | |
|---|---|
| *G01B 21/20* | (2006.01) |
| *A61B 5/11* | (2006.01) |
| *A61B 5/06* | (2006.01) |
| *G01B 3/10* | (2006.01) |

(52) U.S. Cl.

CPC .......... *A61B 5/1077* (2013.01); *A61B 5/1118* (2013.01); *A61B 5/6898* (2013.01); *G01B 21/20* (2013.01); *G01B 2003/1092* (2013.01); *H04M 2250/12* (2013.01)

(56) References Cited

U.S. PATENT DOCUMENTS

| | | | |
|---|---|---|---|
| 2009/0018463 A1 | 1/2009 | Tamura et al. | |
| 2011/0295144 A1 | 12/2011 | Murakawa et al. | |
| 2012/0289833 A1* | 11/2012 | Kashima ................. | A61B 8/14 600/445 |
| 2014/0121564 A1* | 5/2014 | Raskin ................. | A61B 5/0022 600/587 |

FOREIGN PATENT DOCUMENTS

| | | |
|---|---|---|
| JP | 2001-212111 A | 8/2001 |
| JP | 2001212111 A * | 8/2001 |
| JP | 2002-125954 A | 5/2002 |
| JP | 2006-204450 A | 8/2006 |
| JP | 2007-14579 A | 1/2007 |
| JP | 2009-201670 A | 9/2009 |
| JP | 2010-207339 A | 9/2010 |
| JP | 2011-67351 A | 4/2011 |
| JP | 2012-254279 A | 12/2012 |
| JP | 2013-202051 A | 10/2013 |

OTHER PUBLICATIONS

Written Opinion of the International Searching Authority; PCT/JP2014/003305; dated Aug. 19, 2014; with concise explanation.

Japanese Office Action; JP2014-534846; dated Sep. 16, 2014; with concise explanation.

S.Saito; "A Method for Visceral Fat Area Estimation from Abdominal Profile Shape"; IEICE The Institute of Electronics, Information and Communication Engineers; vol. J92-D, No. 11; pp. 2059-2066.

The extended European search report issued by the European Patent Office dated Dec. 19, 2016, which corresponds to European Patent Application No. 14813597.3-1657; 8pp.

Notification of the First Office Action issued by the State Intellectual Property Office of China dated Jun. 1, 2017, which corresponds to Chinese Patent Application No. 201480034328.3 and is related to U.S. Appl. No. 14/389,659; with English language translation.

An Office Action issued by the Japanese Patent Office on Nov. 14, 2017, which corresponds to Japanese Patent Application No. 2014-249207 and is related to U.S. Appl. No. 14/389,659; with English language concise explanation.

* cited by examiner

FIG. 8

| Record number | Time (second) | Orientation information (degree) | Motion information (cm/sec$^2$) | Moving amount (cm) |
|---|---|---|---|---|
| R0 | 0 | 0.00 | 0.00 | 0.00 |
| R1 | T1 | 2.05 | 0.85 | 0.42 |
| R2 | T2 | 3.10 | 1.52 | 1.40 |
| R3 | T3 | 5.81 | 2.65 | 3.25 |
| ⋮ | ⋮ | ⋮ | ⋮ | ⋮ |
| Rn | Tn | 360.00 | 0.00 | 82.05 |

FIG. 16

| Record number | Time (second) | Orientation information (degree) | Motion information (Moving amount) (cm) |
|---|---|---|---|
| R0 | 0 | 0.00 | 0.00 |
| R1 | T1 | 1.01 | 0.41 |
| R2 | T2 | 1.50 | 0.82 |
| R3 | T3 | 0.51 | 1.23 |
| ⋮ | ⋮ | ⋮ | ⋮ |
| Rn | Tn | 360.00 | 82.05 |

| Record number | Time (second) | Orientation information (degree/sec) | Orientation (degree) | Motion information (Moving amount) (cm) |
|---|---|---|---|---|
| R0 | 0 | 0.00 | 0.00 | 0.00 |
| R1 | t1 | 8.22 | 1.37 | 0.42 |
| ⋮ | ⋮ | ⋮ | ⋮ | ⋮ |
| R(n/4) | T(n/4) | 48.72 | 90 | 20.50 |
| ⋮ | ⋮ | ⋮ | ⋮ | ⋮ |
| R(n/2) | T(n/2) | 0.44 | 180 | 41.00 |
| ⋮ | ⋮ | ⋮ | ⋮ | ⋮ |
| R(n/2+a) | T(n/2+a) | 38.21 | 190.12 | 43.15 |

|  |  | Subcutaneous fat area B (cm$^2$) | | | | |
| --- | --- | --- | --- | --- | --- | --- |
|  |  | ~50 | 51~100 | 101~150 | 151~200 | 201~ |
| Visceral fat area A (cm$^2$) | ~50 | P11 | P12 | P13 | P14 | P15 |
|  | 51~100 | P21 | P22 | P23 | P24 | P25 |
|  | 101~150 | P31 | P32 | P33 | P34 | P35 |
|  | 151~200 | P41 | P42 | P43 | P44 | P45 |
|  | 201~ | P51 | P52 | P53 | P54 | P55 |

METHOD, APPARATUS, AND SYSTEM FOR ESTIMATING BODY FAT

CROSS REFERENCE TO RELATED APPLICATIONS

This application claims priority to and the benefit of Japanese Patent Application No. 2013-128266 filed on Jun. 19, 2013, Japanese Patent Application No. 2013-180320 filed on Aug. 30, 2013, Japanese Patent Application No. 2013-246574 filed on Nov. 28, 2013, and PCT/JP2014/000460 filed on Jan. 29, 2014, the entire contents of which are incorporated herein by reference.

TECHNICAL FIELD

The present invention relates to a method, an apparatus, and a system for estimating body fat.

BACKGROUND ART

A growth in metabolic syndrome (hereinafter, referred simply to as "MS") has become a social problem. In Japan, "visceral fat type obesity" is a mandatory field for determination of the MS. A determining method using visceral fat area obtained by computed tomography (hereinafter, referred simply to as "CT") or a circumference of the waist as a reference of the visceral fat type obesity has been proposed. Only limited facilities may conduct the CT. The visceral fat type obesity is determined with reference to the circumference of the waist. However, the determination on the visceral fat type obesity with reference to the circumference of the waist has room for improvement in accuracy.

As such, quantification of the visceral fat area without using the CT has been attempted. Patent Document 1 discloses a visceral fat measuring apparatus that may operate an abdominal morphometric unit, which is a combination of an encoder for measuring a distance and an angular velocity meter, along a periphery of the abdomen and thereby obtain a two-dimensional shape of the abdomen from a measured value. That is, from an abdominal area obtained from the two-dimensional shape of the abdomen and a subcutaneous fat distribution measured by an ultrasonic apparatus, a visceral fat amount is measured.

Also, Non-Patent Document 1 discloses a method of measuring a three-dimensional shape of the abdomen by using two range finders and estimating the visceral fat area from an abdominal cross-sectional shape at a navel position.

RELATED ART DOCUMENTS

Patent Document

Patent Document 1: Japanese Patent Application Laid-Open Publication No. 2001-212111

Non-Patent Document

Senichi Saito and two others, "Method of estimating visceral fat area from abdominal cross-sectional shape", IEICE journal. D, Information System, Nov. 1, 2009, J92-D(11), p. 2059-2066

SUMMARY OF INVENTION

Technical Problem

However, as described in paragraph [0040] of Patent Document 1, a measurement unit needs to be moved around the abdomen to measure an abdominal shape. Therefore, there has been a problem that it is difficult for a user to measure the abdominal shape by moving his/her hand around the body.

Also, Non-Patent Document 1, in order to estimate the visceral fat, needs to obtain an accurate abdominal cross-sectional shape around the abdomen. To that end, it is necessary to use two stationary range finders. Therefore, it is unpractical for an individual, for his/her health management, to measure the abdominal shape and estimate the visceral fat area on a daily basis.

An object of the present invention in light of the above problems is to provide a method, an apparatus, and a system capable of estimating a body fat area of the abdomen based on a portion of an abdominal outline measured by a simple method.

Solution to Problem

In order to solve the above problems, a method of estimating the body fat according to the present invention includes: a step of obtaining orientation information and motion information of an apparatus itself; a step of calculating a portion of an abdominal outline by a control unit, based on the orientation information and the motion information; and a step of estimating, based on the calculated portion of the abdominal outline, at least one of a visceral fat area and a subcutaneous fat area of an abdominal cross-section.

Preferably, there is a further step of controlling a display by the control unit to display an image of the abdominal cross-section corresponding to at least one of the visceral fat area and the subcutaneous fat area that are estimated.

In order to solve the above problems, also, a method of estimating a body fat according to the present invention includes: a step of obtaining orientation information and motion information of an apparatus itself; a step of calculating a portion of an abdominal outline by a control unit, based on the orientation information and the motion information; a step of calculating shape characteristics of the portion of the abdominal outline; and a step of estimating, based on the shape characteristics, an abdominal cross-sectional circumference.

Preferably, there is a further step of carrying out correction by the control unit such that the abdominal outline forms a continuous closed curve, based on the portion of the abdominal outline.

Preferably, there is a further step of estimating, when the portion of the abdominal outline is shorter than a predetermined portion of the abdominal outline, based on a portion of the abdominal outline that is shorter than the predetermined portion of the abdominal outline and suitable for the estimation, at least one of a visceral fat area and a subcutaneous fat area of the abdominal cross-section.

In order to solve the above problems, also, an apparatus according to the present invention includes: a first sensor for obtaining orientation information of the apparatus itself; a device for obtaining motion information of the apparatus itself; and a display for displaying an image of an abdominal cross-section corresponding to at least one of a visceral fat area and a subcutaneous fat area of the abdominal cross-section estimated based on a portion of an abdominal outline calculated based on the orientation information and the motion information.

Preferably, the first sensor may include an orientation sensor, an angular velocity sensor, or an inclination sensor.

Preferably, the device may include a second sensor for obtaining the motion information of the apparatus itself.

Preferably, the second sensor may include an acceleration sensor or an electronic tape measure.

Preferably, the device may include a timer.

Preferably, the apparatus may further include a sound generation unit for generating sound at predetermined intervals while the device is obtaining the motion information.

Preferably, when a predetermined range of the orientation information is not obtained, the display is prevented from displaying the image of the abdominal cross-section.

Preferably, the apparatus may further include a control unit which, by using the orientation information and the motion information obtained after the apparatus has a predetermined posture ready for a measurement, calculates the portion of the abdominal outline.

In order to solve the above problems, further, a system according to the present invention includes: a probe; a first sensor for obtaining orientation information of the probe; a device for obtaining motion information of the probe; and a control unit for estimating, based on a portion of an abdominal cross-section calculated based on the orientation information and the motion information, at least one of a visceral fat area and a subcutaneous fat area of the abdominal cross-section.

Effect of the Invention

According to the present invention, based on the portion of the abdominal outline obtained by a simple method, a body fat area of the abdomen may be estimated.

BRIEF DESCRIPTION OF DRAWINGS

FIG. 8 illustrates exemplary records of orientation information and motion information according to the embodiments of the present invention;

FIG. 16 illustrates exemplary records of the orientation information and the motion information according to the second embodiment of the present invention;

DESCRIPTION OF EMBODIMENTS

Embodiments of the present invention will be described in detail with reference to the accompanying drawings.

In the present embodiments, a smartphone 1 is employed as an example of an apparatus, and the human abdomen is used as an example of an object.

First Embodiment

A smartphone 1 as an apparatus itself includes at least a first sensor unit for obtaining orientation information, a device unit for obtaining motion information, and a controller 10 for calculating a cross-sectional outline of the object. According to the present embodiment, the device unit for obtaining the motion information includes a second sensor unit.

Figure 1:
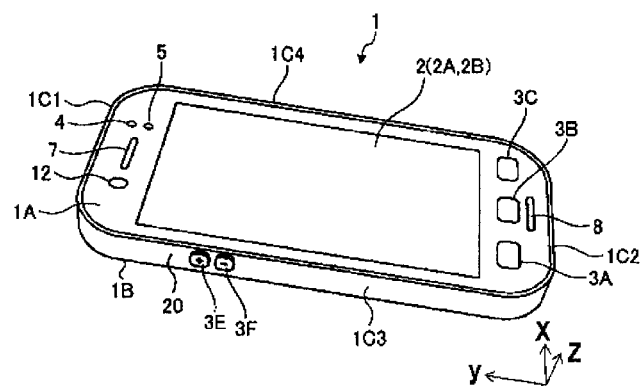
FIG. 1 is a schematic perspective view illustrating an exterior of a smartphone according to embodiments of the present invention.
Figure 2:
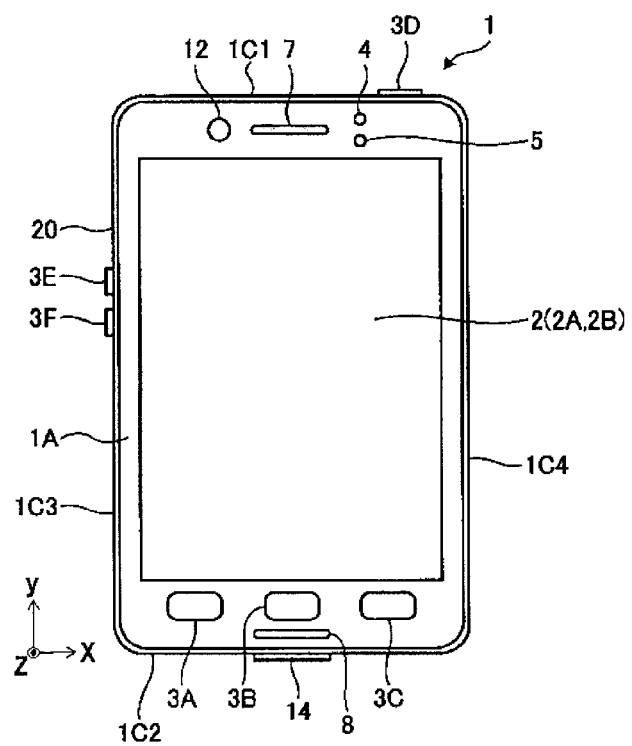
FIG. 2 is a schematic elevation view illustrating the exterior of the smartphone according to the embodiments of the present invention.
Figure 3:
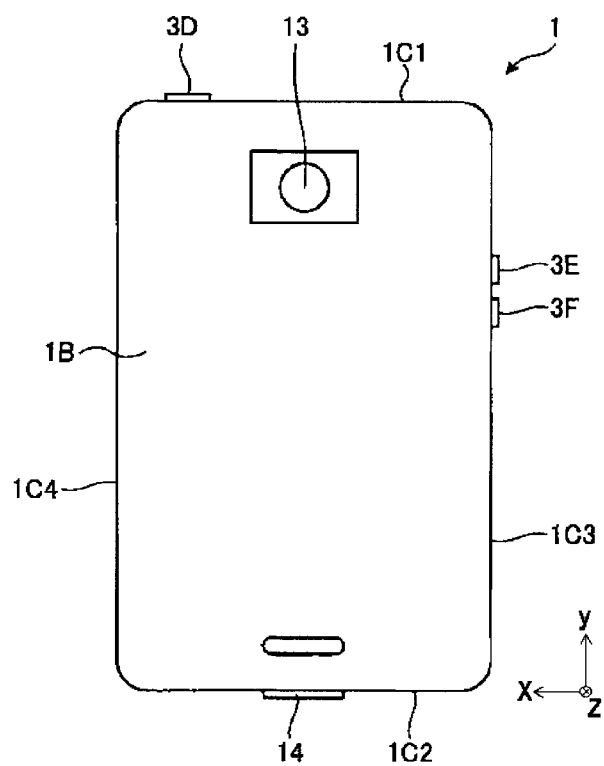
FIG. 3 is a schematic rear view illustrating the exterior of the smartphone according to the embodiments of the present invention.

With reference to FIGS. 1 to 3, an exterior of the smartphone 1 according to a first embodiment will be described.

A housing 20 includes a front face 1A, a rear face 1B, and side faces 1C1 to 1C4. The front face 1A is a front portion of the housing 20. The rear face 1B is a rear portion of the housing 20. The side faces 1C1 to 1C4 are side portions for connecting the front face 1A and the rear face 1B. Hereinafter, the side faces 1C1 to 1C4 may be collectively referred to as a side face 1C without specifying which one of the side faces.

The smartphone 1 includes, on the front face 1A, a touchscreen display 2, buttons 3A to 3C, an illuminance sensor 4, a proximity sensor 5, a receiver 7, a microphone 8, and a camera 12. The smartphone 1 includes a camera 13 on the rear face 1B. The smartphone 1 includes buttons 3D to 3F and a connector 14 on the side face 1C. Hereinafter, the buttons 3A to 3F may be collectively referred to as a button 3 without specifying which one of the buttons.

The touchscreen display 2 includes a display 2A and a touchscreen 2B. The display 2A includes a display device such as a liquid crystal display (Liquid Crystal Display), an organic electro-luminescence panel (Organic Electro-Luminescence panel), or an inorganic electro-luminescence panel (Inorganic Electro-Luminescence panel). The display 2A displays characters, images, symbols, figures and the like.

The touchscreen 2B detects a contact thereto by a finger, a stylus pen and the like. The touchscreen 2B may detect positions of contacts thereto by a plurality of fingers or stylus pens.

The touchscreen 2B may be of any detection type such as a capacitive type, a resistive film type, a surface acoustic wave type (or an ultrasonic type), an infrared type, an electromagnetic induction type, a load detection type and the like. The touchscreen 2B of the capacitive type may detect a contact or an approach by the finger or the stylus pen.

Figure 4:
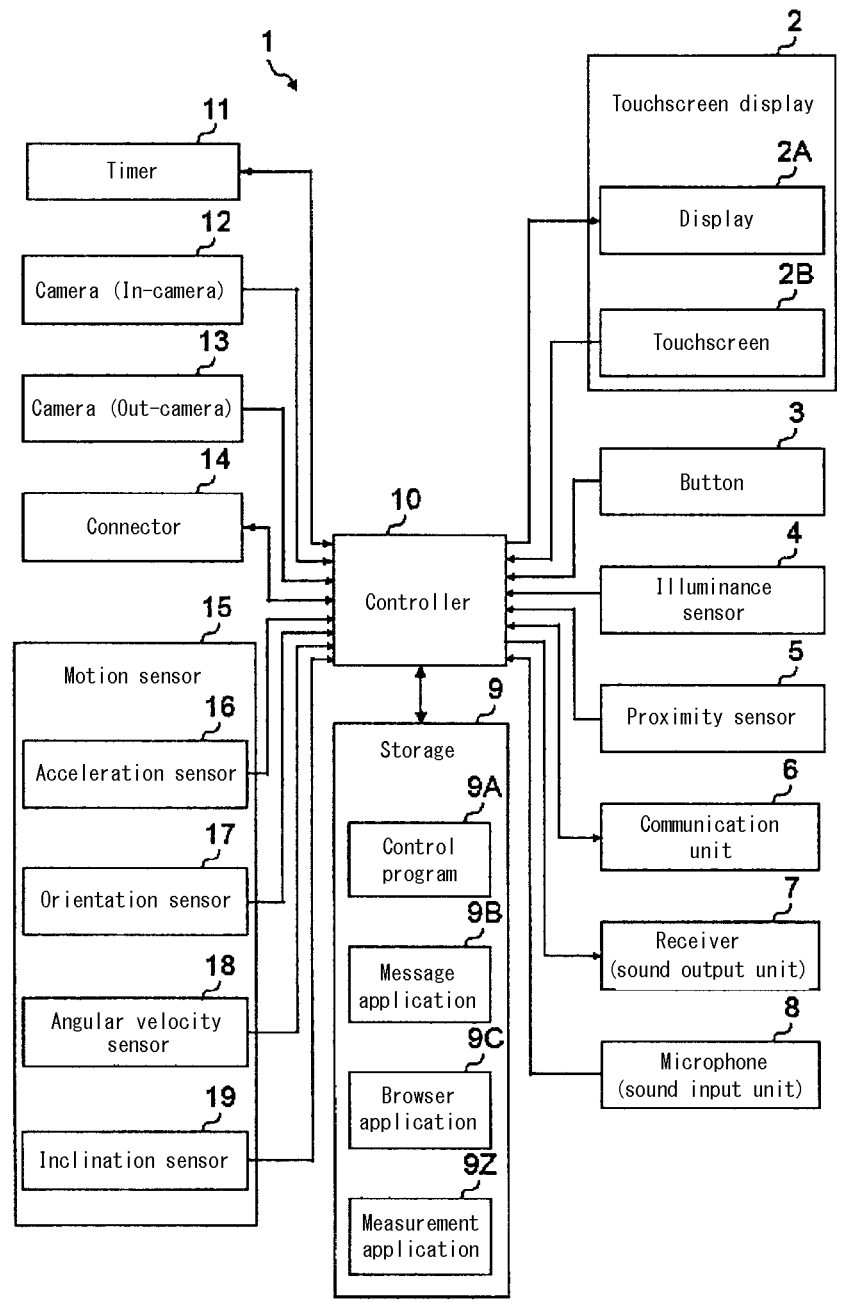
FIG. 4 is a schematic block diagram illustrating functions of the smartphone according to the embodiments of the present invention.

FIG. 4 is a block diagram illustrating a configuration of the smartphone 1. The smartphone 1 includes the touchscreen display 2, the button 3, the illuminance sensor 4, the proximity sensor 5, a communication unit 6, the receiver 7, the microphone 8, a storage 9, the controller 10, a timer 11, the cameras 12 and 13, the connector 14, and a motion sensor 15.

The touchscreen display 2, as described above, includes the display 2A and the touchscreen 2B. The display 2A displays the characters, the images, the symbols, and the figures. The touchscreen 2B receives a contact to a reception region as an input. That is, the touchscreen 2B detects the contact. The controller 10 detects a gesture to the smartphone 1. The controller 10, in corporation with the touchscreen 2B, detects an operation (the gesture) to the touchscreen 2B (the touchscreen display 2). Also, the controller 10, in corporation with the touchscreen 2B, detects an operation (the gesture) to the display 2A (the touchscreen display 2).

The button 3 is operated by a user. The button 3 includes the buttons 3A to 3F. The controller 10, in cooperation with the button 3, detects an operation to the button. The operation to the button may be, for example, a click, a double click, a push, a long push, or a multi-push.

For example, the buttons 3A to 3C are any one of a home button, a back button, and a menu button. According to the present embodiment, the buttons 3A to 3C are of touch sensor type. For example, the button 3D is a power on/off button of the smartphone 1. The button 3D may also function as a sleep/sleep cancel button. For example, the buttons 3E and 3F are volume buttons.

The illuminance sensor 4 detects illuminance. The illuminance includes, for example, intensity, brightness, and luminance of the light. The illuminance sensor 4 is used for, for example, adjustment of the luminance of the display 2A.

The proximity sensor 5 carries out a non-contact detection of a presence of an object positioned nearby. The proximity sensor 5 detects, for example, the face approaching the touchscreen display 2.

The communication unit 6 carries out a radio communication. A communication method employed by the communication unit 6 conforms to a radio communication standard. As the radio communication standard, there are, for example, communication standards for a cellular phone such as 2G, 3G, and 4G. As communication standards for the cellular phone, there are LTE (Long Term Evolution), W-CDMA, CDMA2000, PDC, GSM (registered trademark), and PHS (Personal Handy-phone System). As the radio communication standard, there are, for example, WiMAX (Worldwide Interoperability for Microwave Access), IEEE802.11, Bluetooth (registered trademark), IrDA, and NFC. The communication unit 6 may support one or more of the foregoing communication standards.

The receiver 7 outputs a voice signal transmitted from the controller 10 as voice. The microphone 8 converts the voice of the user into the voice signal and transmits the voice signal to the controller 10. The smartphone 1 may further include a speaker in place of the receiver 7.

The storage 9 stores programs and data. Also, the storage 9 is used as a work area for temporarily storing a result of processing of the controller 10. The storage 9 may include any storage device such as a semiconductor storage device, a magnetic storage device and the like. Also, the storage 9 may include a plurality of types of the storage devices. Further, the storage 9 may include a combination of a mobile storage medium, such as a memory card, and a storage medium reader.

The programs stored in the storage 9 include an application that runs in the foreground or background and a control program for supporting an operation of the application. The application, for example, controls the display 2A to display a predetermined image and controls the controller 10 to execute the processing based on the gesture detected via the touchscreen 2B. The control program is, for example, OS. The application and the control program may be installed to the storage 9 via the radio communication by the communication unit 6 or via the storage medium.

The storage 9 stores, for example, a control program 9A, a message application 9B, a browser application 9C, and a measurement application 9Z. The message application 9B serves an email function for creation, transmission, reception, and display of email. The browser application 9C serves a WEB browsing function for displaying WEB pages. The measurement application 9Z serves a measuring function that allows the user to measure a cross-sectional outline of the object by using the smartphone 1.

The control program 9A serves a function associated with various controls for operating the smartphone 1. The control program 9A, for example, achieves a call by controlling the communication unit 6, the receiver 7, and the microphone 8. Note that the function served by the control program 9A may be used in combination with a function served by another program such as the message application 9B.

The controller 10 is, for example, CPU (Central Processing Unit). The controller 10 may be an integrated circuit such as SoC (System-on-a-Chip) having another components such as the communication unit 6 and the like integrated therein. The controller 10 may have a structure in which a plurality of integrated circuits are combined. The controller 10 achieves various functions by generally controlling operations of the smartphone 1.

The controller 10, in particular, refers data stored in the storage 9 as necessary. The controller 10 executes an instruction included in the program stored in the storage 9 and controls the display 2A, the communication unit 6, and the motion sensor 15, thereby achieving the various functions. The controller 10 achieves the various functions by executing an instruction included in the measurement application 9Z stored in the storage 9. The controller 10, based on a result of detection by each of detection units such as the touchscreen 2B, the button 3, and the motion sensor 15, may change the control. According to the present embodiment, the controller 10 entirely functions as a control unit. The controller 10, based on the orientation information obtained by the first sensor unit and the motion information obtained by the second sensor unit, calculates the cross-sectional outline of the object.

Figure 14:
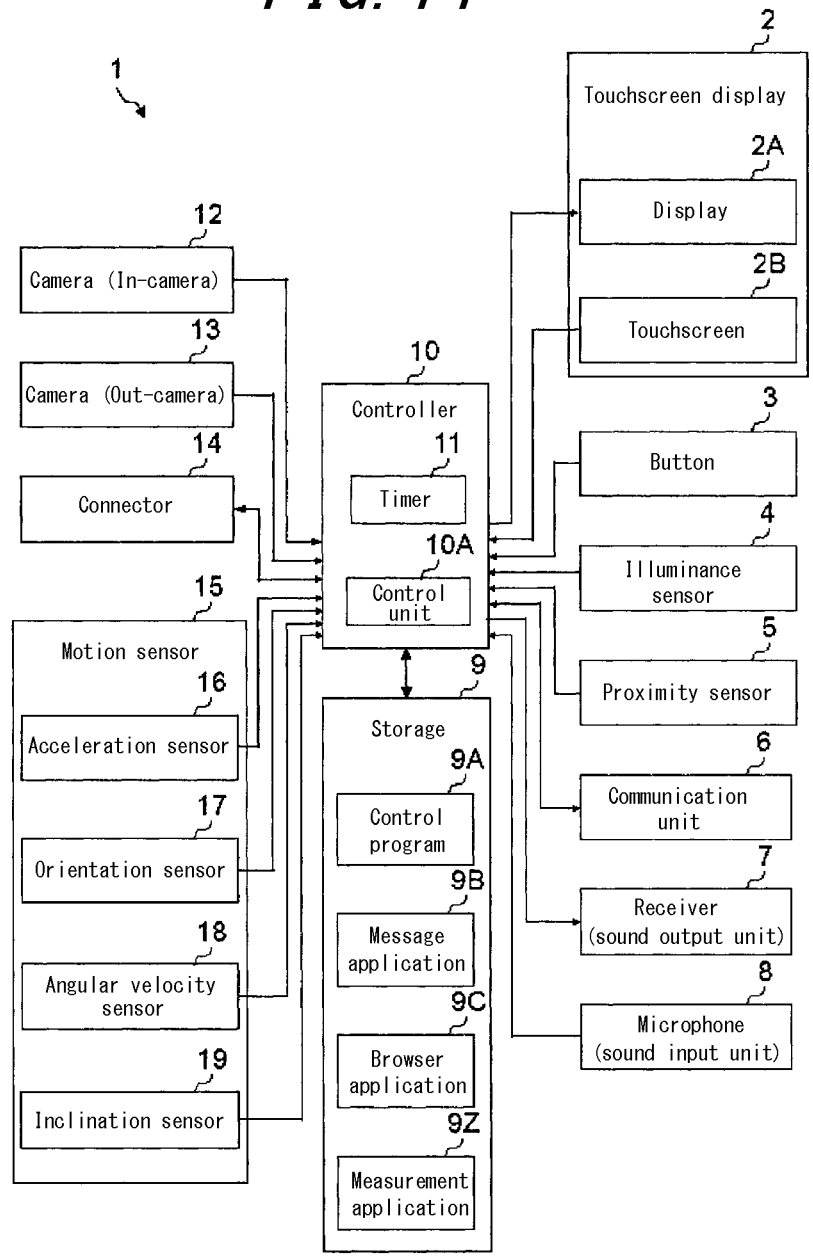
FIG. 14 is a schematic block diagram illustrating functions of the smartphone according to a second embodiment of the present invention.

The timer 11 outputs a clock signal at a predetermined frequency. The timer 11, upon reception of an instruction of timer operation from the controller 10, outputs the clock signal to the controller 10. The first sensor unit and the second sensor unit, based on the clock signal input via the controller 10, obtains the orientation information and the motion information, respectively, for a plurality of times. Note that the timer 11 may be disposed outside the controller 10 or, as illustrated in FIG. 14 described below, contained in the controller 10.

The camera 12 is an in-camera for capturing an object facing the front face 1A. The camera 13 is an out-camera for capturing an object facing the rear face 1B.

The connector 14 is a terminal for connecting to another apparatus. The connector 14 according to the present embodiment also functions as a communication unit for allowing the smartphone 1 to communicate with another apparatus via a connection object connected to the terminal. The connector 14 may be a generic terminal such as USB (Universal Serial Bus), HDMI (registered trademark) (High-Definition Multimedia Interface), MHL (Mobile High-definition Link), Light Peak, Thunderbolt, a LAN connector (Local Area Network connector), and an earphone and/or microphone connector. The connector 14 may be an exclusively designed terminal such as a Dock connector. The apparatus connected to the connector 14 may be, for example, a battery charger, an external storage, a speaker, a communication apparatus, and an information processing apparatus.

The motion sensor 15 detects a motion factor. The motion factor is primarily processed as a control factor of the smartphone 1 itself. The control factor indicates a condition of the smartphone 1 itself and is processed by the controller 10. The motion sensor 15 according to the present embodiment includes an acceleration sensor 16, an orientation sensor 17, an angular velocity sensor 18, and an inclination sensor 19. Outputs from the acceleration sensor 16, the orientation sensor 17, the angular velocity sensor 18, and the inclination sensor 19 may be used in combination. Processing a combination of the outputs of the motion sensor 15 allows the controller 10 to carry out the processing that highly reflects a movement of the smartphone 1 itself.

According to the present embodiment, the first sensor unit obtains orientation information of the smartphone 1 itself. The orientation information of the smartphone is information output from the first sensor unit and associates with an orientation of the smartphone 1. The orientation information of the smartphone 1 includes, for example, a direction of geomagnetism, an inclination with respect to the geomagnetism, a direction of a rotation angle, a change in the rotation angle, a direction of the gravity, an inclination with respect to the gravity and the like.

The orientation of the smart phone 1 refers to a normal direction of a surface of the housing 20 facing the object at the time of measurement of the cross-sectional outline of the object. The surface of the housing 20 made to face the object may be a surface which orientation is detectable by the first sensor unit, and may be any one of the front face 1A, the rear face 1B, and the side faces 1C1 to 1C4.

According to the present embodiment, the orientation sensor 17 is used as the first senor unit. The orientation sensor 17 is a sensor for detecting the direction of the geomagnetism. According to the present embodiment, an element obtained by projecting the orientation of the smartphone 1 on a plane parallel to the ground refers to the orientation information obtained by the orientation sensor 17. The orientation information obtained by the orientation sensor 17 indicates the orientation of the smartphone 1. The orientation of the smartphone 1 may be obtained as directional information of 0 to 360 degrees. For example, the orientation information indicates 0 degree when the smartphone 1 is facing north, 90 degrees when the smartphone 1 is facing west, 180 degrees when the smartphone 1 is facing south, and 270 degrees when the smartphone 1 is facing west. According to the present embodiment, the cross-section of a measurement object parallel to the ground allows the orientation sensor 17 to obtain the orientation information more accurately. According to the present embodiment, since the object is the abdomen, the measurement is preferably carried out while a subject person is standing up.

The orientation sensor 17 outputs a direction of the geomagnetism that is detected. For example, when the direction of the geomagnetism is output as the motion factor, the controller 10 may use the motion factor as the control factor reflecting the orientation of the smartphone 1. For example, when a change in the direction of the geomagnetism is output as the motion factor, the controller 10 may carry out the processing by using the motion factor as the control factor reflecting the change in the orientation of the smartphone 1.

Also, the angular velocity sensor 18 may be used as the first sensor unit. The angular velocity sensor 18 detects an angular velocity of the smartphone 1. The angular velocity sensor 18 may obtain the angular velocity of the smartphone 1 as the directional information. The controller 10, by carrying out time integration of the obtained angular velocity one time, calculates the orientation of the smartphone 1. The calculated orientation of the smartphone 1 corresponds to a relative angle based on an initial value at start of the measurement.

The angular velocity sensor 18 outputs the angular velocity that is detected. For example, when a direction of the angular velocity is output as the motion factor, the controller 10 may use the motion factor as the control factor reflecting a rotational direction of the smartphone 1. For example, when the angular velocity is output, the controller 10 may carry out the processing by using the motion factor as the control factor reflecting a rotation amount of the smartphone 1.

Also, the inclination sensor 19 may be used as the first sensor. The inclination sensor 19 detects gravitational acceleration acting on the smartphone 1. For example, the inclination sensor 19 may obtain the gravitational acceleration of the smartphone 1 as the orientation information. For example, the smartphone 1, through the inclination sensor 19, may obtain the orientation information of −9.8 to 9.8 [m/sec$^2$]. For example, the orientation information of 9.8 [m/sec$^2$] is obtained when a y-axis direction of the smartphone 1 illustrated in FIG. 1 corresponds to a gravity direction, and the orientation information of −9.8 [m/sec$^2$] is obtained when the y-axis direction opposes to the gravity direction. Also, when the y-axis direction is perpendicular to the gravity direction, the orientation information of 0 [m/sec$^2$] is obtained. According to the present embodiment, the cross-section of the measurement object perpendicular to the ground allows the inclination sensor 19 to obtain the orientation information more accurately. When the object is the abdomen, the measurement is preferably carried out while the subject person is lying.

The inclination sensor 19 outputs an inclination that is detected. For example, when an inclination with respect to the gravity direction is output as the motion factor, the controller 10 may carry out the processing by using the motion factor as the control factor reflecting the orientation of the smartphone 1.

The controller 10 may calculate the orientation from the orientation information of the smartphone 1. For example, the angular velocity sensor 18 described above obtains the angular velocity as the orientation information. Based on the obtained angular velocity, the controller 10 calculates the orientation of the smartphone 1. For example, the inclination sensor 19 described above obtains the gravitational acceleration as the orientation information. Based on the obtained gravitational acceleration, the controller 10 calculates the orientation of the smartphone 1 with respect to the gravity direction.

The first sensor unit may use a combination of the motion sensors described above. Processing a combination of the orientation information from a plurality of motion sensors allows the controller 10 to calculate the orientation of the smartphone 1 itself more accurately.

According to the present embodiment, the device unit for obtaining the motion information of the smartphone 1 itself serves as the second sensor unit. The second sensor unit obtains the motion information of the smartphone 1 itself. The motion information of the smartphone 1 refers to information output from the second sensor unit. The motion information of the smartphone 1 refers to information associated with a moving amount of the smartphone 1. The motion information of the smartphone 1 includes, for example, acceleration, speed, and the moving amount.

The moving amount of the smartphone 1 according to the present embodiment refers to a moving amount of a reference position of the housing 20 of the smartphone 1. The reference position of the housing 20 may locate anywhere as long as detectable by the second sensor unit and may locate, for example, on a surface of the side face 1C1.

According to the present embodiment, the acceleration sensor 16 is used as the second sensor. The acceleration sensor 16 is a sensor for detecting acceleration acting on the smartphone 1. The acceleration sensor 16 may obtain the acceleration of the smartphone 1 as the motion information. The controller 10, by carrying out the time integration of the obtained acceleration two times, calculates the moving amount of the smartphone 1.

The acceleration sensor 16 outputs the acceleration that is detected. For example, when a direction of the acceleration is output, the controller 10 may carry out the processing by using the direction of the acceleration as the control factor reflecting a moving direction of the smartphone 1. For example, when the acceleration is output, the controller 10 may use the acceleration as the control factor reflecting a moving speed and the moving amount of the smartphone 1.

The controller 10 calculates the cross-sectional outline of the object. The cross-sectional outline of the object is calculated based on the orientation information and the motion information obtained by the first sensor unit and the second sensor unit. In some cases, the controller 10 may calculate the orientation and the moving amount in the course of the calculation.

Each of the motion sensors 15 described above are capable of detecting the motion factors in three axial directions. The three axial directions detected by the motion sensors 15 according to the present embodiment are substantially orthogonal to one another. An x-direction, a y-direction and a z-direction illustrated in FIGS. 1 to 3 correspond to the three axial directions of the motion sensors 15. The three axial directions do not need to be orthogonal to one another. The motion sensor 15 for detecting the three axial directions that are not orthogonal to one another may calculate a motion factor of three directions that are orthogonal to one another. Each of the motion sensors may have a different reference direction. According to the present embodiment, each of the motion sensors does not need to detect three axial directions. The controller 10, based on the orientation information of one axial direction and the moving information of one axial direction, may calculate the cross-sectional outline.

The first sensor unit and the second sensor unit may use any one of the motion sensors 15 described above or others.

Some or all of the programs stored in the storage 9 as illustrated in FIG. 4 may be downloaded from another apparatus via the radio communication carried out by the communication unit 6. Or, some or all of the programs stored in the storage 9 as illustrated in FIG. 4 may be stored in a storage medium readable by the storage medium reader included in the storage 9. Or, some or all of the programs stored in the storage 9 as illustrated in FIG. 4 may be stored in a storage medium readable by a storage medium reader connected to the connector 14. The storage medium may be, for example, a flash memory, HDD (registered trademark) (Hard Disc Drive), CD (Compact Disc), DVD (registered trademark) (Digital Versatile Disc), and BD (Blu-ray (registered trademark) Disc).

A structure of the smartphone 1 is illustrated in FIGS. 1 to 4 by way of example only and may be appropriately changed within a range that does not impair the gist of the present invention. For example, the number and the type of the button 3 are not limited to the example illustrated in FIG. 1. For example, the smartphone 1, as a button for operations associated with a display, may be provided with a button of a numeric keypad or a QWERTY sequence in place of the buttons 3A to 3C. Alternatively, the smartphone 1 may be provided with one button for the operation associated with the display, or no buttons at all. Although the smartphone 1 of the example illustrated in FIG. 4 is provided with two cameras, the smartphone 1 may have only one camera, or no camera at all. Also, the illuminance sensor 4 and the proximity sensor 5 may be constituted by using one sensor. Although in the example illustrated in FIG. 4 the smartphone 1 includes four types of sensors in order to obtain the orientation information and the motion information of the smartphone 1 itself, the smartphone 1 may have only some of the sensors or other types of sensors.

Next, referring to FIGS. 5 and 6, measurement of the abdominal cross-sectional outline by the smartphone 1 according to the present embodiment will be described.

Figure 5:
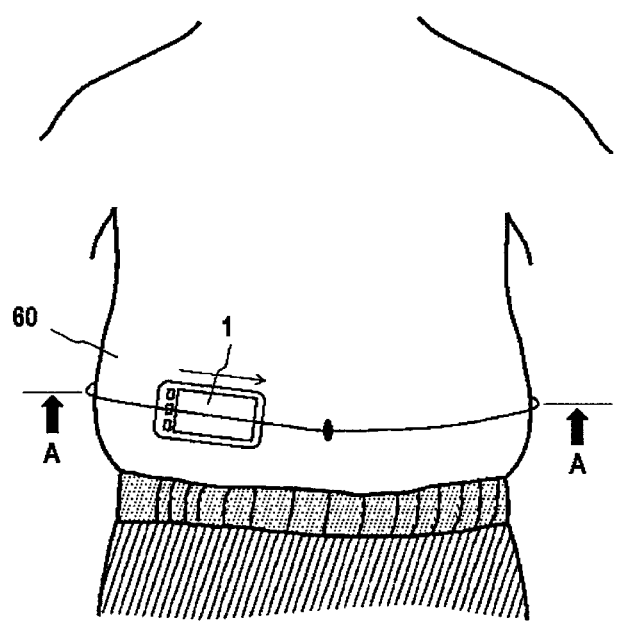
FIG. 5 is a schematic view illustrating measurement of an abdominal cross-sectional outline according to the embodiments of the present invention.

FIG. 5 is a schematic view illustrating the measurement of the abdominal cross-sectional outline according to the present embodiment.

Figure 6:
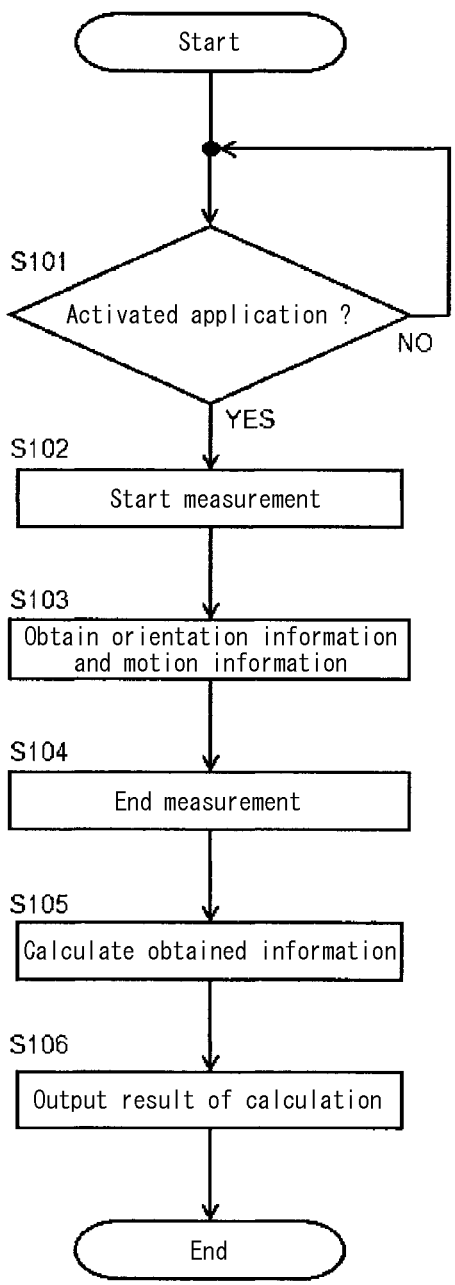
FIG. 6 is a flowchart of measurement of a cross-sectional outline according to the embodiments of the present invention.

FIG. 6 is a flowchart of the measurement of the abdominal cross-sectional outline according to the present embodiment.

At step S101, the user initiates the measurement application 9Z for measuring the cross-sectional outline. At step S102, next, the measurement starts. At the start of the measurement, the smartphone 1 is held against a surface of an abdomen 60 in any position on the abdomen for measurement of the cross-sectional outline. According to the present embodiment, the cross-sectional outline at the height of the user's navel (an A-A position in FIG. 5) is measured. Within a range that does not hinder the measurement of the cross-sectional outline, the smartphone 1 may directly, or via clothing, contact the surface of the abdomen 60. The measurement may start at any position on the A-A position of the abdomen upon a starting action preset to the smartphone 1. The starting action may be pressing any one of the buttons 3 of the smartphone 1, or tapping a certain position on the touchscreen 2B. The plane of the smartphone 1 contacting the surface of the abdomen may be any one of the front face 1A, the rear face 1B, and the side faces 1C1 to 1C4. In consideration of operability, however, the rear face 1B is used as the plane contacting the surface of the abdomen according to the present embodiment.

At step S103, the user moves the smartphone 1 along the A-A position on the surface of the abdomen 60 and makes the circuit of the abdomen 60. Here, the smartphone 1 is moved at a constant speed while contacting the surface of the abdomen 60. Accordingly, each of the information may be obtained at constant intervals, and accuracy in the measurement of the outline is improved.

At step S103, under pre-programed conditions, the orientation sensor 17 obtains the orientation information, and the acceleration sensor 16 obtains the motion information. The orientation information and the motion information are obtained for a plurality of times. The orientation information and the motion information are obtained according to the crock signal output from the timer 11. Depending on a size and complexity of the cross-section of the measurement object, the interval to obtain each information is appropriately selected. The interval to obtain the information is appropriately selected from, for example, sampling frequencies of 5 to 60 Hz. The orientation information and the motion information that are obtained are temporality stored with in the smartphone 1. This measurement is continually executed from the start at step S102 to an end at step S104.

The user, when the smartphone 1 has made the circuit of the abdomen 60 while contacting the surface thereof, carries out an ending action preset to the smartphone 1 and thereby ends the measurement (step S104). The ending action may be pressing any one of the buttons 3 of the smartphone 1 or tapping a certain position on the touchscreen 2B. Or, when the orientation information obtained by the orientation sensor 17 of the smartphone 1 corresponds to the orientation information at the start of the measurement, or when the orientation information has changed by 360 degrees from the orientation information at the start of the measurement, the smartphone 1 may automatically recognize that the smartphone 1 has made the circuit of the abdomen 60 and end the measurement. When the smartphone 1 carries out such automatic recognition, the user does not need to carry out the ending action, and thereby the measurement is more simplified.

The smartphone 1, at step S105, calculates the orientation information and the motion information obtained at step S103. Those calculations are carried out by the controller 10. The controller 10 calculates the abdominal cross-sectional outline and an abdominal circumference of the user. The calculations carried out at step S105 will be described in detail below.

The smartphone 1, at step S106, outputs results of the calculations carried out at step S105. The output of the results of the calculation takes a variety of manners such as, for example, to be displayed on the display 2A, to be transmitted to a server, and the like. The smartphone 1 ends the flow when finishing outputting the results of the calculations of the abdominal cross-sectional outline and the abdominal circumference.

According to the present embodiment, the smartphone 1 is moved in the y-axis direction while the rear face 1B is contacting the abdomen. In such a case, the orientation sensor 17 may be a one-axis sensor capable of measuring the orientation of the smartphone 1 in the y-axis direction. The acceleration sensor 16 may be a one-axis sensor capable of measuring the moving amount of the smartphone 1 in the y-axis direction.

Next, with reference to FIGS. 7 to 9, the method of calculating the cross-sectional outline will be described by using the smartphone 1 as an example.

FIG. 7 illustrate examples of the direction and the moving amount according to the present embodiment.

Figure 7A:
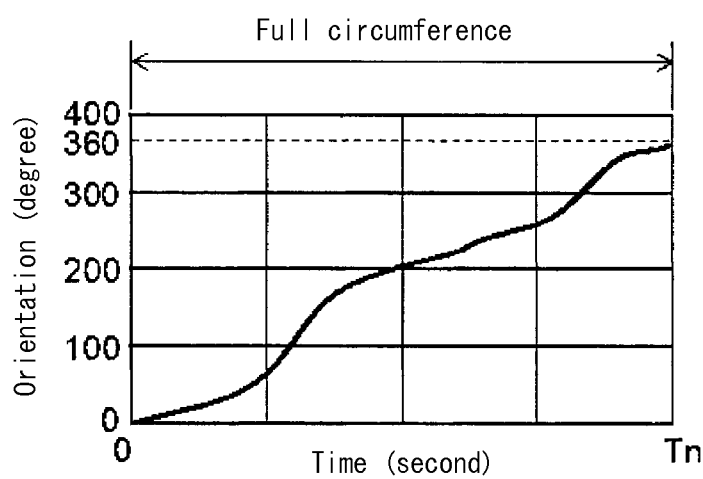
FIG. 7A illustrates an example of orientation according to the embodiments of the present invention.
Figure 7B:
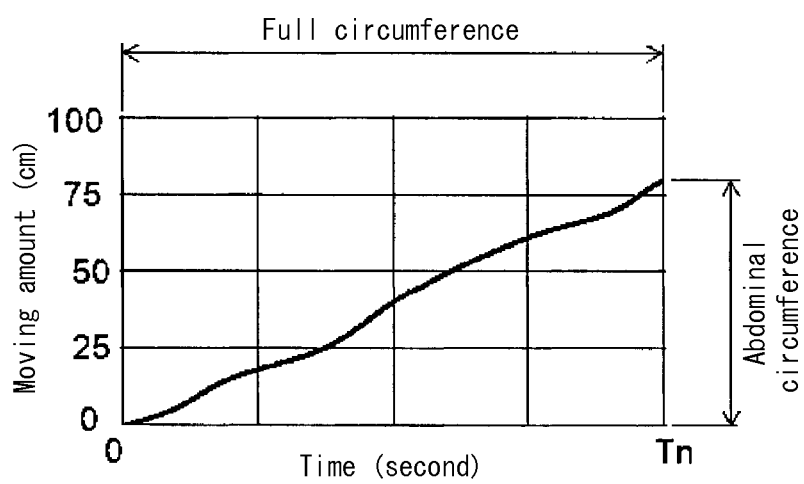
FIG. 7B illustrates an example of a moving amount according to the embodiments of the present invention.

Horizontal axes in FIGS. 7A and 7B represent time for the start of the measurement to the end of the measurement. The time is counted according to the clock signal output by the timer 11. When the abdominal circumference is measured in Tn seconds, it means that the measurement starts at 0 second and ends at Tn seconds. The smartphone 1, between 0 to Tn seconds, obtains the orientation information and the moving information at predetermined intervals.

In FIG. 7A, the horizontal axis represents the time, and a vertical axis represents the orientation of the smartphone 1. The orientation of the smartphone 1 represented by the horizontal axis corresponds to the orientation information obtained by the orientation sensor 17. According to the present embodiment employing the orientation sensor 17 as the first sensor unit, the orientation information represents the orientation of the smartphone 1. The orientation of the smartphone 1 is represented by an angle at 0 to 360 degrees. When the orientation of the smartphone 1 has changed by 360 degrees from an original angle thereof at the start of the measurement, it is determined that the smartphone 1 has made the circuit of the abdomen. According to the present embodiment, for simplification, the original angle at the start of the measurement is set to 0 degree, and thus the angle after the smartphone 1 has made the circuit of the abdomen is at 360 degrees.

In FIG. 7B, the horizontal axis represents the time, and the vertical axis represents the moving amount of the smartphone 1. The moving amount of the smartphone 1 represented by the vertical axis is calculated based on the motion information obtained by the acceleration sensor 16. The motion information of the smartphone 1 according to the present embodiment refers to acceleration data obtained by the acceleration sensor 16. The moving amount is calculated by the controller 10 by carrying out the time integration of the acceleration data two times. When the acceleration data have a large noise, digital filter processing may be carried out. As a digital filter, there are a low-pass filter, a band pass filter and the like. The moving amount of the smartphone 1 at the end of the measurement corresponds to a circumference of the measurement object, which is the abdominal circumference according to the present embodiment. Preferably, the abdominal circumference is calculated in consideration of a position of the acceleration sensor 16 within the smartphone 1. According to the present embodiment, that is, the moving amount is preliminarily corrected in consideration of a distance between the rear face 1B, which is the plane brought into contact with the surface of the abdomen 60, and the acceleration sensor 16. Thereby, the abdominal circumference is calculated accurately.

Although according to the present embodiment the orientation and the moving amount are measured at the same time Tn, the orientation and the moving amount may be measured at different times Ta and Tb, respectively. In this case, preferably, the horizontal axis in FIG. 7A uses a standardized time 0-1 standardized by Ta while the horizontal axis in FIG. 7B uses a standardized time 0-1 standardized by Tb, and the horizontal axes in FIGS. 7A and 7B have the same values.

FIG. 8 is exemplary records made up of the obtained information.

The start of the measurement is represented by a record number R0, and the end of the measurement is represented by a record number Rn. Each record includes a combination of the orientation information and the motion information corresponding to the time. Each record also includes the moving amount calculated based on the motion information. According to the present embodiment employing the orientation sensor, the orientation information represents the orientation of the smartphone 1. The orientation and the moving amount calculated based on the combination of the orientation information and the motion information correspond to information obtained at the same time in FIGS. 7A and 7B, or information obtained at the same standardized time. Intervals between the times of the records does not need to be equal. Also, although each record preferably includes the information obtained at the same time from the viewpoint of the accuracy of the measurement of the cross-sectional outline, a small time difference may be allowed. When there is a time difference, the controller 10 may ignore the time difference, or calculate information corresponding to another time from one record.

Figure 9:
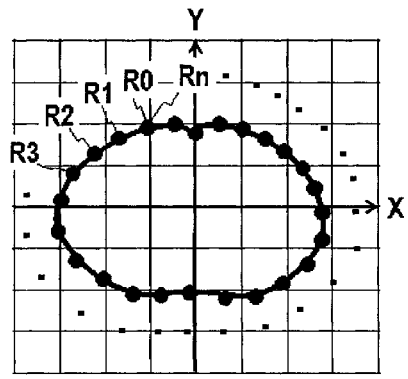
FIG. 9 is a diagram illustrating a calculated cross-sectional outline according to the embodiments of the present invention.

FIG. 9 is a diagram illustrating the calculated cross-sectional outline.

Plotting from the obtained record R0 to the record Rn in order according to the orientation and the moving amount allows calculation of the cross-sectional outline of the object. To aid in understanding, the R0 to the Rn in the figure represent corresponding record numbers. Also, each dots on the solid line represents a position of each of the records. Although the solid line has more dots in practice, some of the dots are omitted for the purpose of clarity of the figure.

The calculation of the cross-sectional outline is carried out as follows. First, the R0 is set to any point. Next, the position of the R1 is calculated from the change in the moving amount between the record R0 and the record R1 and the orientation information of the record R1. Then, a position of R2 is calculated from the change in the moving amount between the record R1 and the record R2 and the orientation information of the record R2. This calculation is carried out to Rn, and the position of R0 to a position of Rn is connected in order. Thereby the cross-sectional outline of the object is calculated and displayed.

Figure 10:
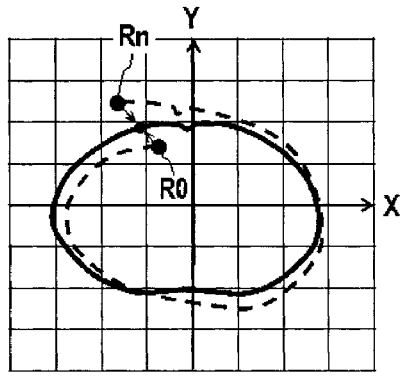
FIG. 10 is a diagram illustrating correction of the calculated cross-sectional outline according to the embodiments of the present invention.

FIG. 10 is a diagram illustrating correction of the calculated cross-sectional outline.

The orientation sensor and the acceleration sensor have a measurement error. As a result, the motion of the smartphone 1 may deviate from the A-A position, and the cross-sectional outline as indicated by a dotted line in FIG. 10 is calculated. This result of the calculation of the cross-sectional outline is inaccurate because R0 as a measurement start point and Rn as a measurement end point do not meet each other. In this case, offset is carried out such that the measurement start point R0 and the measurement end point Rn meet each other, thereby correcting the error. Further, to each of the records between the measurement start point R0 and the measurement end point Rn, small offset is carried out as correction.

Figure 11:
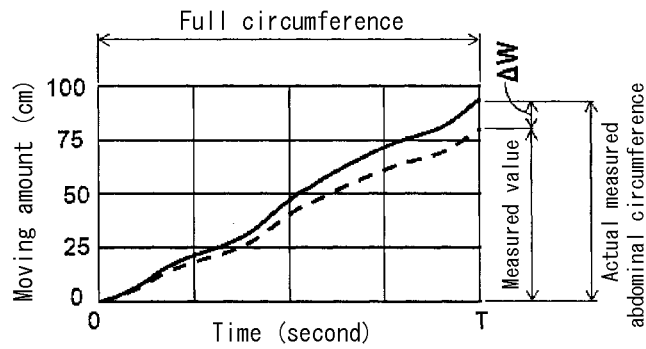
FIG. 11 is a diagram illustrating correction based on an actual measured value according to the embodiments of the present invention.

FIG. 11 is a diagram illustrating correction by using the actual measured value according to the present embodiment.

Although in the above embodiment calculation of the cross-sectional outline uses the motion information obtained by the acceleration sensor 16, when an actual measured value of the circumference of the object preliminarily measured by another means is available, the cross-sectional outline may be calculated more accurately. In FIG. 11, the horizontal axis and the vertical axis represent the time and the moving amount, respectively. In the figure, the dotted line represents the moving amount calculated based on the motion information obtained by the acceleration sensor 16. The moving amount at the end of the measurement corresponds to the circumference of the measurement object, which is the abdominal circumference. The moving amount at the end of the measurement is corrected to meet the actual measured value of the abdomen preliminarily measured by means of a tape measure or the like. In particular, a correction amount $\Delta W$ illustrated in FIG. 11 is offset, and then an inclination of a graph is corrected according to the $\Delta W$ that has been offset. A solid line represents corrected data. By using the record of the corrected data represented by the solid line, the controller 10 calculates the cross-sectional outline of the object.

Next, correction of the inclination of the calculated cross-sectional outline and the position that are calculated will be described. When the orientation of the smartphone 1 at the start of the measurement is set to 0 degree, an axis of symmetry of the calculated cross-sectional outline may be inclined. As for the abdominal cross-sectional outline, for example, it may be wished to correct the inclination and display the abdomen or the back facing the Y-axis direction in FIG. 9. In order to correct the inclination with respect to coordinate axes illustrated in FIG. 9, the cross-sectional outline may be rotated so as to minimize or maximize a width of the cross-sectional outline in the X-axis direction or a width of the cross-sectional outline in the Y-axis direction.

Also, when a position coordinate of the smartphone 1 at the start of the measurement locates at an XY origin in FIG. 9, the calculated cross-sectional outline is displayed being displaced from the center. Correction of such a displacement of the abdominal cross-sectional outline may be wished so as to display the XY origin of FIG. 9 and the center of the abdominal cross-sectional outline that are meeting each other. For correction of the position, an intersection of a center line of the width of the cross-sectional outline in the X-axis direction and a center line of the width of the cross-sectional outline in the Y-axis direction is moved to the XY origin.

As described above, the apparatus of the present embodiment may measure the cross-sectional outline of the object by using the sensors integrated in the smartphone 1. The smartphone 1 is smaller than measurement equipments such as CT. The smartphone 1 may measure the cross-sectional outline in a short time. Also, the smartphone 1 allows the user to measure himself/herself in a simple manner. Also, the smartphone 1, unlike the equipments such as the CT and the like, may be easily carried. Also, the smartphone 1 allows the user to store the data and thereby facilitates viewing a daily change. Further, the smartphone 1 involves a less risk of radiation exposure during measurement.

Figure 12:
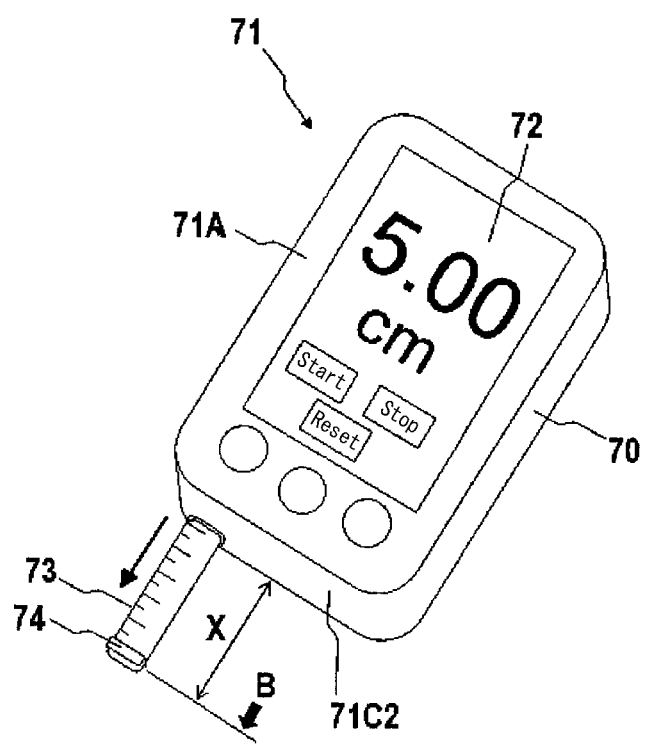
FIG. 12 is a schematic view illustrating an electronic tape measure according to the embodiments of the present invention.

FIG. 12 is a schematic diagram illustrating the electronic tape measure according to the present embodiment.

The electronic tape measure functions to measure a length of the tape that is pulled out and obtain data, thereby obtaining the motion information in a manner similar to the acceleration sensor. The electronic tape measure may be built in the smartphone 1.

An electronic tape measure 71 includes a housing 70. A front face 71A of the housing 70 includes a touchscreen display 72. A side face 71C2 of the housing 70 includes a tape measure 73. The tape measure 73 is provided with scales. The tape measure 73 is normally wound inside the housing 70. The tape measure 73 is provided with a stopper 74 at a leading end thereof. Before measurement, the stopper 74 is placed outside the housing 70 having a B plane of the stopper 74 and the side face 71C2 in contact with each other. In order to measure the object, the stopper 74 is pulled in a direction indicated by an arrow in FIG. 12 in such a manner to pull out the tape measure 73 from the housing 70. At this time, an amount X of the tape measure 73 drawn out from the side face 71C2 as a reference is digitally displayed in the touchscreen display 72. In the embodiment illustrated in FIG. 12, the amount X is 5.00 cm.

When the electronic tape measure 71 is used as the second sensor unit of the smartphone 1 of the present embodiment, a measurement process and a calculation of the cross-sectional outline conform to those described with reference to FIGS. 5 to 9. The following is a description of the measurement process using the electronic tape measure. At start of the measurement at step S102, the housing 70 is brought into contact with the surface of the abdomen. At step S103, while maintaining the stopper 74 at a measurement start position, the user moves the housing 70 along the A-A position on the surface of the abdomen 60 and makes the circuit of the abdomen 60. When the side face 71C2 and the B plane of the stopper 74 meet each other, the measurement ends (step S104).

When the acceleration sensor is used as the second sensor unit, the acceleration is obtained as the motion information. In contrast, when the electronic tape measure is used as the second sensor unit, the moving amount may be directly obtained as the motion information, thereby allowing more accurate measurement of the abdominal circumference.

Next, an example of classification of the calculated abdominal cross-sectional outline will be described.

Figure 13A:
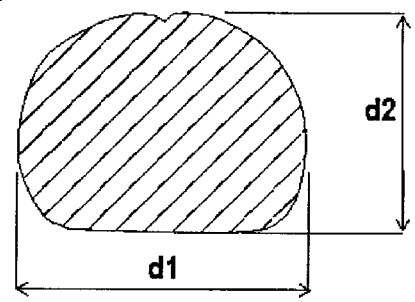
FIG. 13A is a schematic view illustrating an example of classification of the abdominal cross-sectional outline according to the embodiments of the present invention.
Figure 13B:
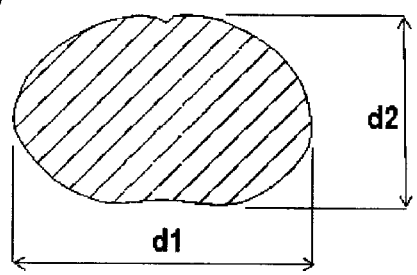
FIG. 13B is a schematic view illustrating an example of classification of the abdominal cross-sectional outline according to the embodiments of the present invention.
Figure 13C:
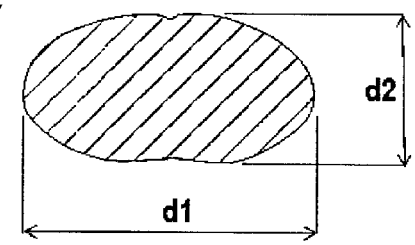
FIG. 13C is a schematic view illustrating an example of classification of the abdominal cross-sectional outline according to the embodiments of the present invention.

FIG. 13 is an example of the classification of the cross-sectional abdominal outline according to the present embodiment.

The smartphone 1 preliminarily stores the classification of the abdominal cross-sectional outline. The classification of the abdominal cross-sectional outline illustrated in FIG. 13 includes (a) visceral obesity type, (b) subcutaneous fat type, and (c) normal type. The user, based on an aspect ratio of the measured abdominal cross-sectional outline (d2/d1 in FIG. 13), is classified into one of the above (a) to (c). For example, the user with the aspect ratio of 0.8 or more is classified into the (a) visceral obesity type, while the user with the aspect ratio of 0.6 to 0.8 (exclusive of 0.8) is classified into the (b) subcutaneous fat type, and the user with the aspect ratio of less than 0.6 is classified into the (c) normal type. In this case, after step S106 of the flowchart illustrated in FIG. 6, a step S107 for "Classification" is added. According to further detailed classifications, the user may obtain determination and advice.

Second Embodiment

FIG. 14 is a block diagram illustrating a configuration of the smartphone 1 according to a second embodiment.

According to the present embodiment, the timer 11 and the control unit 10A are included in the controller 10. The timer 11 serves as the device unit for obtaining the motion information of the smartphone 1. The timer 11, upon reception of an instruction to operate the timer from the control unit 10A, outputs the clock signal. The orientation sensor 17, according to the clock signal output from the timer 11, obtains the orientation information for a plurality of times. The orientation information obtained according to the clock signal is temporality stored in the smartphone 1 together with clock information. Here, the clock information refers to information representing time of obtainment of the orientation information. For example, when periodical clock signals are used, the clock information may indicate a record number representing an obtainment order. The clock information may indicate the time of obtainment of the orientation information. According to the present embodiment, the timer 11 is included in the controller 10, and a timer circuit serving as a functional part of the controller 10 may be used as the timer 11. Further, the present invention is not limited thereto but, as described above with reference to FIG. 4, the timer 11 may be provided outside the controller 10.

The control unit 10A estimates the motion information of the smartphone 1 from the clock information. The motion information of the smartphone 1 refers to information associated with the moving amount of the smartphone 1, and is the moving amount according to the present embodiment. The control unit 10A, based on the orientation information and the motion information, calculates the cross-sectional outline of the object. Hereinafter, features of the present embodiment different from those of the first embodiment will be described, omitting features of the present embodiment the same as those of the first embodiment.

Figure 15:
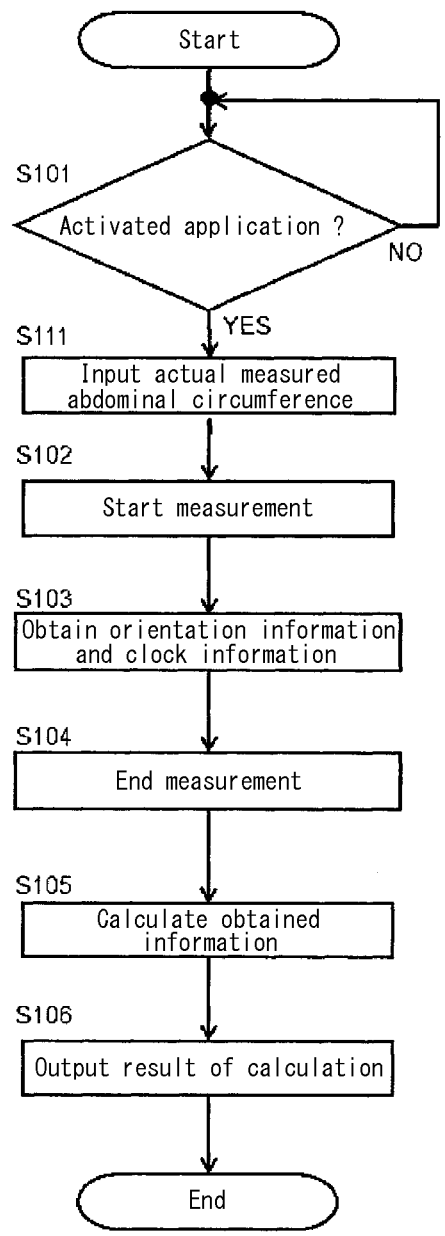
FIG. 15 is a flowchart of measurement of the cross-sectional outline according to the second embodiment of the present invention.

FIG. 15 is a flowchart of the measurement of the abdominal cross-sectional outline according to the second embodiment.

At step S101, the user activates the measurement application 9Z for the measurement of the cross-sectional outline. After the measurement application 9Z is activated, the user inputs the actual measured value of the abdominal circumference measured by the tape measure and the like to the smartphone 1 (step S111). Or, from user information preliminarily stored in the storage 9 of the smartphone 1, the actual measured value of the abdominal circumference may be retrieved. Note that the actual measured value of the abdominal circumference does not need to be input before the start of the measurement (step S102) but may be input after the end of the measurement (step S104).

Next, the measurement starts at step S102. At the start of the measurement, the smartphone 1 is brought into contact with the surface of the abdomen 60 at any position of the abdomen for measurement of the cross-sectional outline. The present embodiment illustrates the measurement of the cross-sectional outline at the height of the naval of the user (the A-A position in FIG. 5). The measurement may start from any position on the A-A position upon the starting action preset to the smartphone 1. At step S103, the user moves the smartphone 1 along the A-A position on the surface of the abdomen 60. The smartphone 1 is moved at a constant speed while contacting the surface of the abdomen 60. To aid the user to move the smartphone at a constant speed, an auxiliary device for assisting the movement of the smartphone may be used. Or, the smartphone 1 may output an auxiliary sound at a constant speed for aiding the movement.

At step S103, the smartphone 1, under the pre-programed conditions, obtains the orientation information by using the orientation sensor 17. The orientation information is obtained for a plurality of times according to the clock signal output from the timer 11. The orientation information obtained according to the clock signal is stored in the smartphone 1 together with the clock information. The measurement is continually executed from the start at step S102 to the end at step S104.

The user, while maintaining the contact of the smartphone 1 to the surface of the abdomen 60, moves the smartphone 1 at a constant speed to make at least the circuit of the abdomen 60. Then, the user carries out the ending action preset to the smartphone 1 and thus ends the measurement (step S104). Or, when the orientation information obtained by the orientation sensor 17 of the smartphone 1 corresponds to the orientation information at the start of the measurement, the smartphone 1 may automatically recognize that the smartphone 1 has made the circuit of the abdomen 60 and end the measurement. Or, when the orientation information has changed by 360 degrees from the orientation information at the start of the measurement, the smartphone 1 may automatically recognize that the smartphone 1 has made the circuit of the abdomen 60 and end the measurement. When the smartphone 1 carries out such automatic recognition, the user does not need to carry out the ending action, and thereby the measurement is more simplified.

At step S105, the control unit 10A, from the actual measured value of the user's abdominal circumference and the clock information obtained at step S103, estimates the moving amount as the motion information of the smartphone 1. Since the moving amount of the smartphone 1 when the smartphone 1 has made the circuit of the user's abdomen is equal to the actual measured value of the abdominal circumference input at step S111 and, also, the smartphone 1 is considered to move at a constant speed, the moving amount as the motion information of the smartphone 1 may be calculated. The control unit 10A, based on the obtained orientation information and the calculated motion information, calculates the cross-sectional outline of the object.

The smartphone 1, at step S106, outputs the result of the calculation carried out at step S105. The smartphone 1, after finishing the output of the results of the calculations of the abdominal cross-sectional outline and the abdominal circumference, ends the flow. Note that other processing, which detailed descriptions are omitted in the flow of the present embodiment, conform to the processing described with reference to FIG. 6.

FIG. 16 is exemplary records of the obtained information according to the second embodiment.

The record number at the start of the measurement is set to R0, and the record number at the end of the measurement is set to Rn. For each of the records, a combination of the orientation information and the motion information corresponding to the time is stored. The motion information corresponds to the moving amount estimated from the record number (or the time) as the clock information. As the motion information of the record number Rn, the actual measured value of the user's abdominal circumference is stored. Since time intervals of each of the records are equal to one another and, also, the smartphone 1 is considered to move at a constant speed, the time intervals between each of the moving amount as the motion information are equal to one another as well. The records thus obtained are displayed as a diagram illustrating the cross-sectional outline.

Plotting from the record R0 to the record Rn that are obtained on the XY coordinate in order according to the orientation and the moving amount allows the calculation of the cross-sectional outline of the object. According to the present embodiment, on the calculated cross-sectional outline illustrated in FIG. 9, each of the plot points are positioned equally spaced apart. During the measurement, when the smartphone 1 is moved at a constant speed, the calculated cross-sectional outline forms a shape symmetrical to the Y-axis. During the measurement, when the smartphone 1 does not move at a constant speed, the calculated cross-sectional outline forms an irregular shape asymmetric to the Y-axis. When the shape of the calculated cross-sectional outline is greatly asymmetric, the smartphone 1 may display a message urging re-measurement at a constant speed. A magnitude of the asymmetry may be determined based on a difference of the plot points in each region separated by the Y-axis in FIG. 9. For example, when the difference of the plot points is other than ±10%, it is determined that the cross-sectional outline is greatly asymmetric. A method of the determination of the magnitude of the asymmetry is not limited thereto but the magnitude may be determined by, for example, calculating areas surrounded by the cross-sectional outline and comparing sizes of the areas. Also, a determination criteria may be appropriately set.

According to the present embodiment, as described above, since the timer is used as the device unit for obtaining the motion information of the smartphone 1 itself, the motion information may be obtained without using the second sensor unit. Therefore, the number of components of the smartphone 1 of the present embodiment may be reduced. Further, the smartphone 1 of the present embodiment allows a reduction in a measurement error due to inaccuracy of the second sensor unit.

Third Embodiment

According to a third embodiment, from a portion of the cross-sectional outline that is calculated, the visceral fat area and the subcutaneous fat area are estimated. Further, based on those estimated values, an image of the abdominal cross-section is displayed in the smartphone 1. The smartphone 1 according to the present embodiment may have the configuration illustrated in the block diagram of FIG. 14 the same as the second embodiment. Hereinafter, features of the third embodiment different from the features of the first and second embodiments will be described, omitting features the same as those of the first and second embodiments.

The storage 9 stores a visceral fat area estimation equation and a subcutaneous fat area estimation equation that are preliminarily created. The storage 9 also stores a plurality of images of the abdominal cross-section. Those images of the abdominal cross-section are classified based on a combination of the visceral fat area and the subcutaneous fat area.

The control unit 10A calculates a portion of the cross-sectional outline of the object and extracts a characteristic coefficient thereof. The control unit 10A retrieves the visceral fat area estimation equation and the subcutaneous fat area estimation equation stored in the storage 9 and, from the extracted characteristic coefficient of the outline, estimates the visceral fat area and the subcutaneous fat area. Further, the control unit 10A extracts one of the plurality of images of the abdominal cross-section stored in the storage 9 and controls the display 2A to display the extracted image.

Although the storage 9 and the control unit 10A of the smartphone 1 are used for the operation according to the present embodiment, the present invention is not limited thereto. A storage and a control unit installed in the server connected to a network may be used to carry out a part of, or all of the operation described above.

According to the present embodiment, the angular velocity sensor 18 obtains the orientation information of the smartphone 1. The timer 11 operates to obtain the motion information of the smartphone 1. However, the present invention is not limited thereto but may use the orientation sensor or the inclination sensor so as to obtain the orientation information. Also, in order to obtain the motion information, the acceleration sensor or the electronic tape measure may be used.

Figure 17:
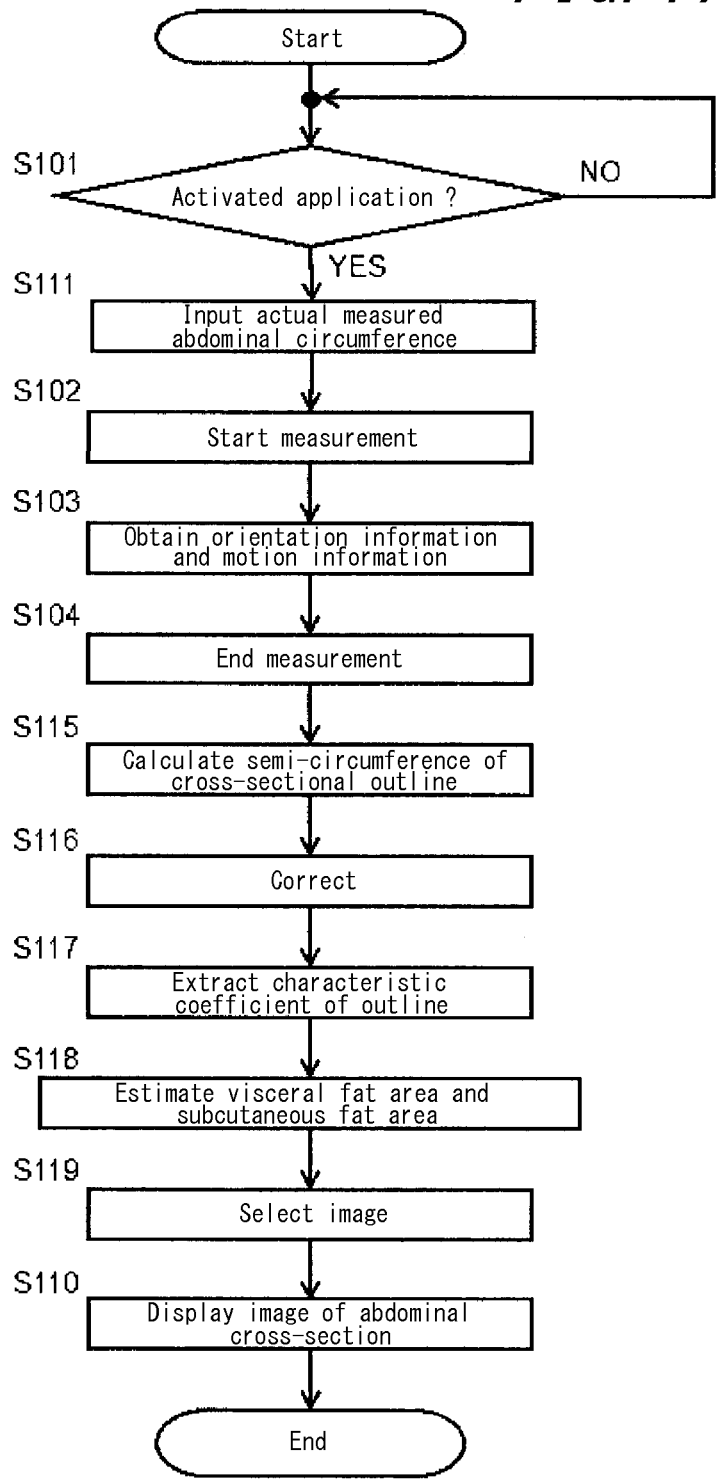
FIG. 17 is a flowchart illustrating an example of processing before displaying an image of the abdominal cross-section according to a third embodiment of the present invention.

FIG. 17 is a flowchart illustrating an example of an operation flow before displaying the image of the abdominal cross-section according to the third embodiment. According to the present embodiment, as an example of calculation of at least a portion of the abdominal cross-sectional outline, calculation of the outline of an approximate semi-circumference portion from the naval will be described.

At step S101, the user activates the measurement application 9Z for the measurement of the cross-sectional outline. After the measurement application 9Z is activated, the user inputs the actual measured value of the abdominal circumference, which is preliminarily measured by the tape measure and the like, to the smartphone 1 (step S111). Or, the actual measured value of the abdominal circumference may be retrieved from the user information preliminarily stored in the storage 9 of the smartphone 1. Note that the processing at step S111 does not need to be carried out before the start of the measurement but may be carried out after the end of the measurement at step S104.

Next, the measurement starts at step S102. At the start of the measurement, the smartphone 1 is brought into contact with the surface of the abdomen 60 at the naval position. A measurement starting position is appropriately selected based on a portion of the abdominal cross-sectional outline to be calculated. Predetermining the measurement starting position prevents change of a range of the outline to be calculated between users, thus reducing errors of the characteristic coefficient of the outline described below. According to the present embodiment, the naval position is set to be the measurement starting position. For example, the measurement starts when the side face 1C1 of the smartphone 1 is brought to meet the naval position. The user carries out the starting action preset to the smartphone 1 to start the measurement.

At step S103, the user moves the smartphone 1 along the A-A position on the surface of the abdomen 60. The smartphone 1 is moved at a constant speed while contacting the surface of the abdomen 60.

At step S103, the smartphone 1, under the pre-programmed conditions, obtains the angular velocity (degree/second) as the orientation information by using the angular velocity sensor 18. The orientation information is obtained for a plurality of times according to the clock signal output from the timer 11. The orientation information obtained according to the clock signal is stored in the smartphone 1 together with obtainment time information. This measurement is continually executed from the start at step S102 to the end at step S104.

The user moves the smartphone 1 by at least a semi-circumference of the abdomen 60 at a constant speed while maintaining the contact of the smartphone 1 to the surface of the abdomen 60. According to the present embodiment, the semi-circumference represents a motion from the naval to the center of the back. When the smartphone 1 is moved by an amount shorter than the semi-circumference, the calculation of the outline becomes incomplete, possibly causing an error of the characteristic coefficient of the outline described below. Accordingly, the smartphone 1 preferably has means to inform the user when the smartphone 1 has moved by the semi-circumference.

When the smartphone 1 is moved by at least the semi-circumference, the user carries out the ending action preset to the smartphone 1, and thereby ends the measurement (step S104). Alternatively, provided that the processing at step S115 described below is executed at the same time, the smartphone 1 may automatically recognize that the smartphone 1 has moved by the semi-circumference when the orientation of the smartphone 1 has changed by 180 degrees from the orientation at the start of the measurement, and end the measurement. When the smartphone 1 carries out such automatic recognition, the user does not need to carry out the ending action, and thereby the measurement is more simplified.

After or during the measurement, the control unit 10A calculates the semi-circumference of the abdominal cross-sectional outline (step S115). The control unit 10A, by carrying out integration of the angular velocity obtained at S103 one time, calculates the orientation of the smartphone 1.

Figures 18, 19:
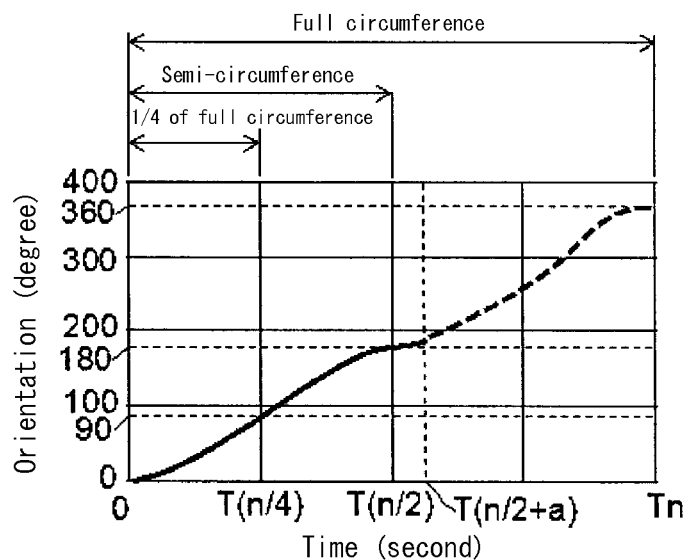
FIG. 18 is a diagram illustrating an example of orientation of a smartphone 1 according to the third embodiment of the present invention.
FIG. 19 illustrates exemplary records made up of obtained information according to the third embodiment of the present invention.

FIG. 18 illustrates an example of the orientation of the smartphone 1 according to the third embodiment. With reference to the figure, a method to extract information about the semi-circumference from the obtained orientation information will be described. The horizontal axis represents the time; the measurement starts at 0 second and ends at T(n/2+a) seconds. Here, n represents the circumference for 360 degrees, and a represents an angle calculated by subtracting the semi-circumference for 180 degrees from the orientation at the end of the measurement. The vertical axis represents the orientation of the smartphone 1. A solid line in the figure represents obtained information, and a dotted line represent a virtual line representing unobtained information about a rest of the circumference. A flat portion of a curved line in the figure around the orientation of 180 degrees is estimated as information about the back and, at a midpoint of the flat portion, it is determined that the smartphone 1 has passed the center of the back, and the semi-circumference is detected. That is, a record from 0 second to T(n/2) seconds in the figure is extracted as the information about the semi-circumference. This method of extracting the information about the semi-circumference portion is described by way of example only. For example, when the flat portion is displaced from 180 degrees, normalization to set the flat portion to 180 degrees may be carried out. Or, normalization may be carried out to set information about a position where the orientation is displaced from the flat portion by 180 degrees to a start point. Or, instead of the midpoint of the flat portion, information about a position with a minimum inclination of the curve near the orientation of 180 degrees may be determined as the center of the back.

FIG. 19 illustrates exemplary records including obtained and normalized information according to the third embodiment. The start point of a semi-circumferential outline (the naval position according to the present embodiment) that is extracted is represented by the record number R0, an end point of the semi-circumferential outline (a record of the center of the back with the orientation of 180 degrees according to the present embodiment) is represented by the record R (n/2), and last acquired information is represented by record R (n/2+a). Each record stores a combination of the orientation information and the motion information. The motion information refers to the moving amount estimated from the record number (or the time) as the clock information. According to the present embodiment, the record of the orientation of 0 to 180 degrees is extracted as information about the semi-circumference. As the motion information of the record number R(n/2), a value of a half of the actual measured value of the user's abdominal circumference is stored. Since the intervals of each of the records are equal to one another and the smartphone 1 is considered to move at a constant speed, each of the moving amounts as the motion information are at equal intervals as well. The record thus obtained is shown in a table showing the semi-circumferential outline of the cross-section. Plotting the obtained record R0 to the record R (2/n) in order on the XY coordinate according to the orientation and the moving amount allows the calculation of the semi-circumference of the cross-sectional outline of the object. Note that step S115 may be executed in parallel with step S103.

The smartphone 1, at step S116, corrects the result of the calculation carried out at the step S115. This correction is pre-processing of extraction of the characteristic coefficient of the outline executed at the next step S117. The characteristic coefficient of the outline fluctuates depending on the orientation and the position of the outline on any XY coordinate system. According to the present embodiment, the orientation of the outline refers to an orientation of the axis of symmetry described below, and the position of the outline refers to a position of the midpoint described below. By correcting the orientation, position and the like of the outline, a fluctuation in the characteristic coefficient of the outline caused based on measurement conditions may be reduced. The correction of the orientation and the position of the outline may be easily carried out for the semi-circumference of the calculated cross-sectional outline, based on an inverting closed curve replicated on a line serving as the axis of symmetry, which is connecting the start point (the naval position according to the present embodiment) and the end point (the center of the back according to the present embodiment). In order to correct the orientation of the outline, the inverting closed curve is rotated such that the axis of symmetry thereof (the line connecting the naval and the center of the back) faces a predetermined direction. In order to correct the position of the outline, the inverting closed curve is moved such that a midpoint thereof meets the origin of the coordinate system. The orientation and the position of the outline may be corrected by conventionally known methods.

Figures 20, 21:
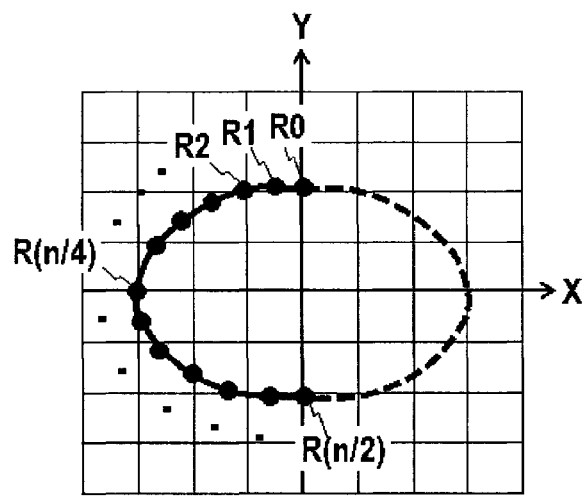
FIG. 20 is a diagram illustrating a cross-sectional outline calculated and corrected according to the third embodiment of the present invention.
FIG. 21 illustrates an example of a classification table of the image of the abdominal cross-section according to the third embodiment of the present invention.

FIG. 20 is a diagram illustrating the cross-sectional outline that is calculated and corrected according to the third embodiment. In the figure, a solid line represents the semi-circumference of the cross-sectional outline that is calculated, and a dotted line represents an imaginary curve obtained by inverting the semi-circumference of the calculated cross-sectional outline with respect to the axis of symmetry. Black dots represent the obtained records plotted on the XY coordinate.

The smartphone 1, after correction at step S116, extracts the characteristic coefficient of the semi-circumference of the cross-sectional outline (step S117). As a method of extracting characteristics of a shape of the curve, there is a method to obtain a curvature function and the like. According to the present embodiment, however, a method using Fourier analysis will be described. By using the Fourier analysis to the curve of the semi-circumference of the cross-sectional outline or to the inverting closed curve, Fourier coefficient may be obtained. As is well known, the Fourier coefficient of each order obtained by the Fourier analysis to the curve is used as a coefficient indicating characteristics of a shape. Which order of Fourier coefficients is set as the characteristic coefficient is determined at the time of creation of each estimation equation described in detail below. According to the present embodiment, Fourier coefficients $Sa_1$, $Sa_2$, $Sa_3$, and $Sa_4$ those having influence on the visceral fat area are extracted as the characteristic coefficients of the visceral fat area. Also, Fourier coefficients $Sb_1$, $Sb_2$, $Sb_3$, and $Sb_4$ those having influence on the subcutaneous fat area are extracted as the characteristic coefficients of the subcutaneous fat area. When independent variables of the estimation equation are used as principal components in creation of each of the estimation equations, the principal components may be extracted as the characteristic coefficients.

The smartphone 1 assigns the characteristic coefficients $Sa_1$ to $Sa_4$ and $Sb_1$ to $Sb_4$ to the visceral fat area estimation equation and the subcutaneous fat area estimation equation that are determined in advance, and thereby estimates a visceral fat area A and a subcutaneous fat area B of the user (step S118). Examples of the visceral fat area estimation equation and the subcutaneous fat area estimation equation are shown below as Formula 1 and Formula 2, respectively.

$$A = -483.8 + 46.2 \times Sa_1 - 13.6 \times Sa_2 + 36.8 \times Sa_3 + 43.2 \times Sa_4 \quad \text{[Formula 1]}$$

$$B = -280.0 + 41.6 \times Sb_1 - 24.9 \times Sb_2 + 16.6 \times Sb_3 - 40.0 \times Sb_4 \quad \text{[Formula 2]}$$

Creation methods of the visceral fat area estimation equation and the subcutaneous fat area estimation equation will be described in detail below.

Next, the smartphone 1, based on the visceral fat area A and the subcutaneous fat area B estimated at step S118, selects an image having a highest similarity to the user's abdominal cross-section (step S119).

FIG. 21 illustrates an example of a classification table of the image of the abdominal cross-section according to the third embodiment. The smartphone 1 preliminarily stores the classification table illustrated in FIG. 21. According to the present embodiment, the smartphone 1 stores 25 types of images (P11 to P55) with different visceral fat areas and subcutaneous fat areas. The 25 types of images may be CT images of the abdomen, pictures schematizing those CT images, or marks. From the 25 types of images, one image corresponding to user's estimated visceral fat area A and subcutaneous fat area B is selected.

The selected image is displayed in the display 2A of the smartphone 1 (step S110).

Although in the third embodiment of the present invention all of the steps are carried out by the smartphone 1, the present invention is not limited thereto, but the server connected via the network and the like may execute at least some of the steps. For example, the steps S102 to S104 for measurement and the step S110 for display may be executed by the smartphone 1, while other steps may be executed by the server connected via the network. When the server executes complicated calculations, a speed of the processing from the start to the end may be increased.

According to the third embodiment, also, since the image is displayed, a user's storage state of the visceral fat and the subcutaneous fat may be clearly shown without the necessity to conduct the CT of the abdomen. When the CT image of the abdomen is displayed, the user's estimated abdominal cross-sectional shape may be visualized more realistically, which may be effectively used for guidance of the MS. Also, displaying values of the visceral fat area and the subcutaneous fat area together with the image may inform the user of the user's storage state of the visceral fat and the subcutaneous fat in more detailed manner.

Figure 22:
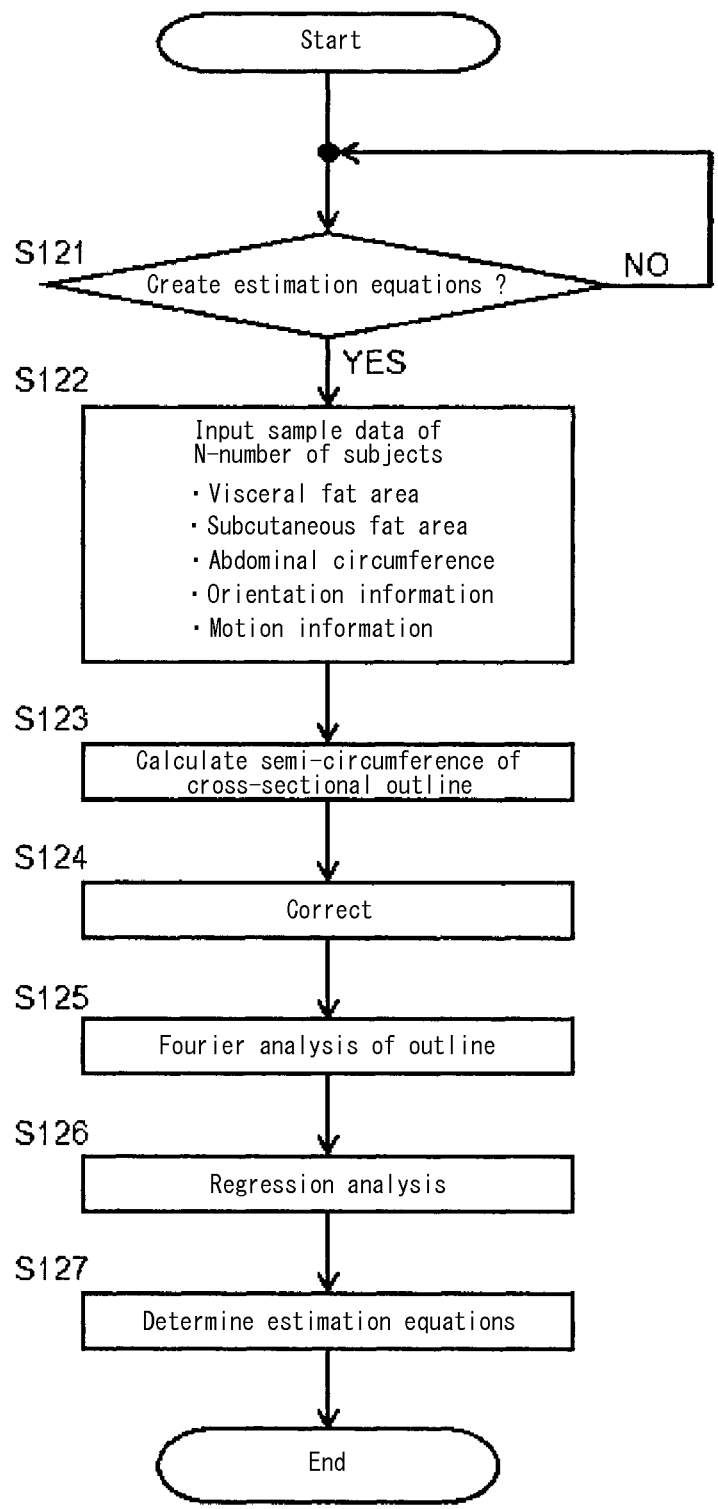
FIG. 22 is a flowchart for creating a visceral fat area estimation equation and a subcutaneous fat area estimation equation according to the third embodiment of the present invention.

FIG. 22 is a flowchart for creation of the visceral fat area estimation equation and the subcutaneous fat area estimation equation according to the third embodiment. With reference to FIG. 22, a process to create Formula 1 and Formula 2 will be described. Note that these estimation equations do not need to be created on the smartphone 1 but may be preliminarily calculated by using other computers and the like. Since the estimation equations are preliminarily created and incorporated in the application, the user does not need to directly create or change the estimation equations.

At step S121, a creator executes creation of the estimation equations. At step S122, the creator inputs preliminarily obtained sample data of a predetermined number of people into the computer. The sample data refer to data obtained from the predetermined number of sample subjects. The sample data of one sample subject includes at least the visceral fat area and the subcutaneous fat area that are obtained by the CT, the abdominal circumference measured by the tape measure and the like, and the orientation information and the motion information obtained by the smartphone 1. Preferably, the predetermined number of sample subjects, for an improvement in accuracy of the estimation equations, is a statistically sufficient number and, simultaneously, is composed of a group having a distribution similar to a visceral fat distribution of the subjects of MS diagnosis.

Next, from the abdominal circumference, and the orientation information and the motion information that have been input, the computer calculates the semi-circumference of the cross-sectional outline (step S123). Further, the computer corrects the semi-circumference of the cross-sectional outline that is calculated (step S124). Since the processing at step S123 and the processing at step S124 correspond to the processing at step S115 and the processing at step S116 described above, respectively, detailed descriptions thereof will be omitted.

Next, the Fourier analysis is carried out to the curve of the semi-circumference of the cross-sectional outline that is corrected, or to the inverting closed curve of the cross-sectional outline (step S125). The Fourier analysis to the curve of the cross-sectional outline allows obtainment of a plurality of Fourier coefficients. As is well known, the Fourier coefficient of each order obtained by the Fourier analysis to a curve is used as a coefficient representing characteristics of a shape. According to the present embodiment, the Fourier analysis is carried out to the sample data of the predetermined number of people, thereby obtaining the Fourier coefficients of the X-axis, the Y-axis, and their 1 to k order (k represents any integer) thereof. Further, for the Fourier coefficients, a well-known principal component analysis may be carried out to reduce the number of order. Note that the principal component analysis is an analytical technique to explore common components in multivariate data (in the present embodiment, a plurality of Fourier coefficients) and create a kind of composite variable (a principal component), which allows expression of the characteristics of the curve with further reduced number of variables.

Then, by using the plurality of Fourier coefficients (or the principal components) that is determined at step S125 and the visceral fat area that is preliminarily input, a regression analysis is carried out (step S126). The regression analysis is one of statistical methods of examining a relationship between a resulting value and a causing value and thus demonstrating the relationship. Using the Fourier coefficients (or the main component) as independent variables and the visceral fat area obtained by the CT as dependent variables, the regression analysis is carried out to the data of the predetermined number of sample subjects, and thus the visceral fat area estimation equation is created. As for the subcutaneous fat area, a similar calculation is carries out to create the subcutaneous fat area estimation equation.

Formula 1 and Formula 2 described above are examples of the estimation equations thus created. Independent variables $Sa_1$, $Sa_2$, $Sa_3$, and $Sa_4$ are the characteristics coefficients for estimation of the user's visceral fat area, and independent variables $Sb_1$, $Sb_2$, $Sb_3$, and $Sb_4$ are the characteristic coefficients for estimation of the user's subcutaneous fat area. Some or all of the characteristic coefficients of the visceral fat area estimation equation $Sa_1$ to $Sa_4$ and the characteristic coefficients of the subcutaneous fat area estimation equation $Sb_1$ to $Sb_4$ may be the same Fourier coefficients. In this way, the visceral fat area estimation equation and the subcutaneous fat area estimation equation may be created by the statistic methods (the principal component analysis, the regression analysis and the like) described above.

Note that although at step S126 the visceral fat area estimation equation and the subcutaneous fat area estimation equation are created by carrying out the regression analysis to the visceral fat area and the subcutaneous fat area, respectively, an abdominal cross-sectional circumference estimation equation may also be created in a similar manner. That is, the regression analysis is carried out by using the plurality of Fourier coefficients (or the principal components) determined at step S125 and the abdominal circumference that is preliminarily input. Then, by using the Fourier coefficients as the independent variables (or the principal components) and the abdominal circumference measured by the tape measure and the like as the dependent variable, the regression analysis is carried out to the data of the predetermined number of sample subjects. Thereby, the abdominal cross-sectional circumference estimation equation may be created.

As described above, since smartphone 1 of the present embodiment may measure the semi-circumference of the abdominal cross-sectional outline in an easy and accurate manner, the visceral fat area and the subcutaneous fat area may be accurately estimated in a short time.

According to the smartphone 1 of the present embodiment, also, since a human's abdominal cross-sectional outline is bilaterally symmetric, calculation of at least the semi-circumference of the abdominal cross-section allows estimation of the visceral fat area and the subcutaneous fat area of the abdominal cross-section. Therefore, the user only needs to move the smartphone 1 by a semi-circle of the abdomen, which shortens the measurement time. Also, since the necessity for the user to pass the smartphone 1 from a hand to the other during the measurement is eliminated, the user may easily move the smartphone 1 at a constant speed. Accordingly, the accuracy in the measurement may be further improved.

Note that, according to the present invention, in addition to the calculation of the semi-circumference, ¼ of a full circumference may also be calculated. Since the human's internal organs locate between the lumbar vertebra to the navel, the visceral fat area around the internal organs is considered to be more related to the outline of the abdominal cross-section on a naval side. Accordingly, the visceral fat area may be estimated by calculating approximate ¼ of the full circumference from the naval to the flank.

For example, the calculation of ¼ of the full circumference from the naval to the flank will be described. As for the operation flow, the "semi-circumference" in the description of the flowchart illustrated in FIG. 17 described above may be replaced with the "¼ of the full circumference". For the calculation of ¼ of the full circumference at step S115, for example, when the orientation of the smartphone 1 is changed by 90 degrees from the start of the measurement, it is determined that the smartphone 1 has moved by ¼ of the full circumference of the abdomen, and the information is extracted. In the graph of the orientation of the smartphone 1 illustrated in FIG. 18 as described above, at the orientation of 90 degrees in the figure it is determined that the smartphone 1 has moved by ¼ of the full circumference of the abdomen, and ¼ of the full circumference is detected. That is, a record from the 0 second to T(n/4) seconds in the figure is extracted as information about ¼ of the full circumference. In FIG. 19 as described above, records between the orientations of 0 to 90 degrees are extracted as the information about ¼ of the full circumference. In the exemplary records illustrated in FIG. 19, an end point of ¼ of the full circumference corresponds to a record R(n/4). For motion information of the record number R(n/4), a quarter of the actual measured value of the user's abdominal circumference is stored. Since the smartphone 1 is moved at a constant speed, the moving amounts as the motion information are at equal intervals as well. Plotting from the record R0 to the record R(n/4) thus obtained in order according to the orientation and the moving amount allows the calculation of ¼ of the full circumference of the cross-sectional outline of the object. The correction of the orientation and the position of the outline at step S116 may be easily carried out to ¼ of the full circumference that is calculated, based on an inverting closed curve replicated with respect to the Y-axis and the X-axis of the coordinate system as the axes of symmetry. Also, the estimation equations illustrated in FIG. 22 as described above are created by replacing the semi-circumference with ¼ of the full circumference. This method of extracting ¼ of the full circumference is described by way of example only; when the orientation is changed by 180 degrees at T(n/2) seconds, records for a half of the time may be extracted as information about ¼ of the full circumference.

According to the smartphone 1 of the present embodiment, the calculation of at least ¼ of the full circumference of the cross-sectional outline allows the estimation of the visceral fat area of the abdominal cross-section. Therefore, the user only needs to move the smartphone 1 by at least ¼ of the circumference of the abdomen, which shortens the measurement time. Also, since the necessity for the user to move the smartphone 1 to the back during the measurement is eliminated, the user may easily move the smartphone 1 at a constant speed. Accordingly, the accuracy in the measurement may be further improved.

Although according to the present embodiment ¼ of the full circumference from the naval to the flank is used as an example, the present invention is not limited thereto. The subcutaneous fat area may be estimated by calculating ¼ of the full circumference from around the flank to the back. Generally, a portion from around the flank to the back carries the subcutaneous fat and thus an outline thereof is less influenced by the visceral fat area. Therefore, this portion is suitably used for estimation of the subcutaneous fat.

Fourth Embodiment

According to a fourth embodiment, from a portion of the cross-sectional outline that is calculated, the visceral fat area, the subcutaneous fat area, and the abdominal cross-sectional circumference are estimated. According to the present embodiment, also when a predetermined abdominal outline (a semi-circumference portion) is not available, the visceral fat area, the subcutaneous fat area, and the abdominal cross-sectional circumference are estimated from information about the abdominal outline for 135 degrees (⅜ of a full circumference). The smartphone 1 according to the present embodiment may have the same configuration as the second embodiment illustrated by the block diagram of FIG. 14. Hereinafter, features of the present embodiment different from those of the first to third embodiments will be described, omitting features the same as those of the first to third embodiments.

The storage 9 in FIG. 14 stores the visceral fat area estimation equation, the subcutaneous fat area estimation equation, and the abdominal cross-sectional circumference estimation equation those are preliminarily created. The storage 9 also stores a plurality of images of the abdominal cross-section. These images of the abdominal cross-section are classified based on the combination of the visceral fat area and the subcutaneous fat area. The control unit 10A calculates a portion of the abdominal outline and extracts the characteristic coefficient thereof. Also, the control unit 10A retrieves the visceral fat area estimation equation, the subcutaneous fat area estimation equation, and the abdominal cross-sectional circumference estimation equation those are stored in the storage 9 and estimates, from the extracted characteristic coefficient of the outline, the visceral fat area, the subcutaneous fat area, and the abdominal cross-sectional circumference. Further, the control unit 10A extracts one of the plurality of images of the abdominal cross-section stored in the storage 9 and controls the display 2A to display the image.

Figure 23:
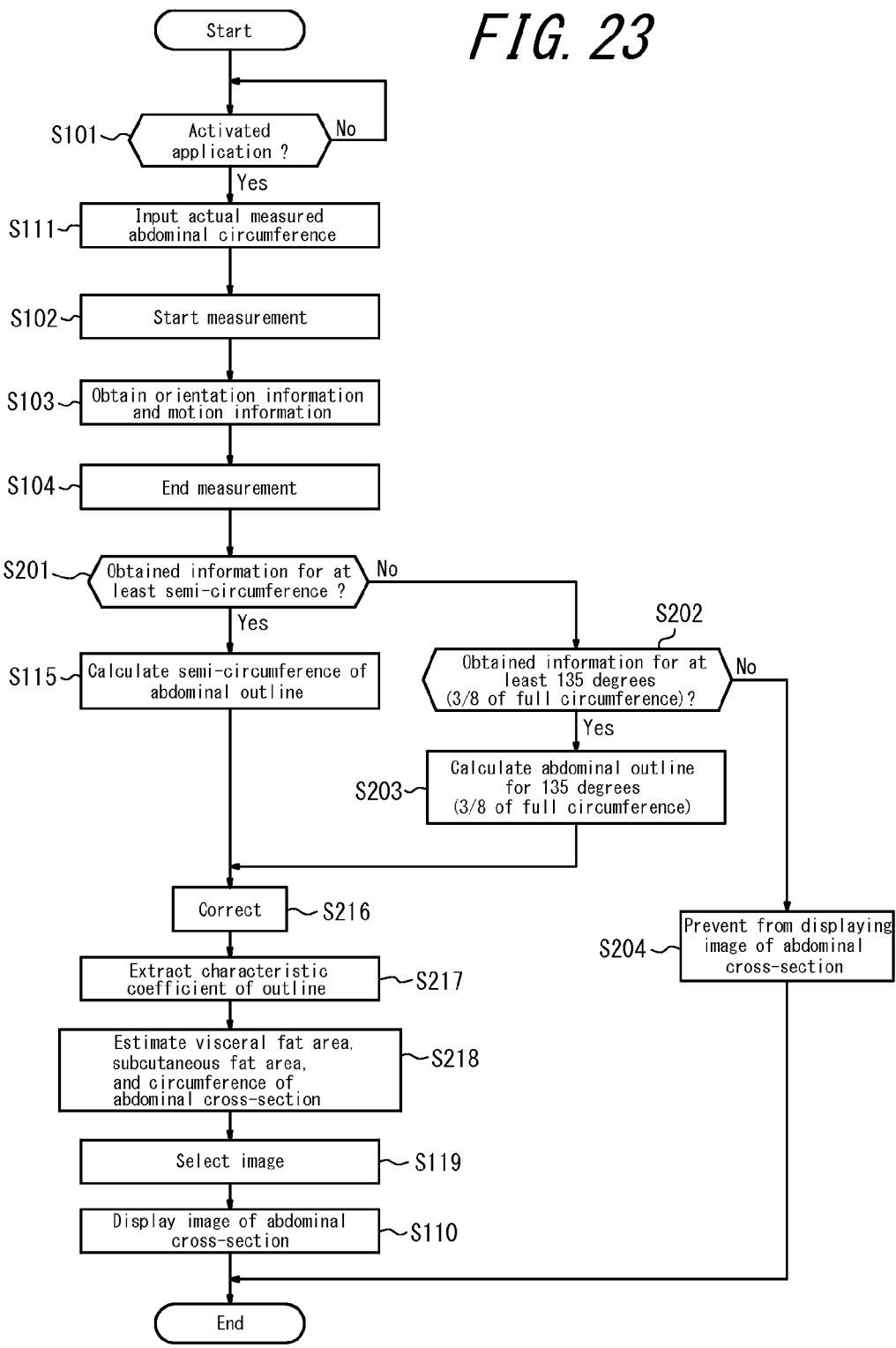
FIG. 23 is a flowchart illustrating an example of processing before displaying the image of the abdominal cross-section according to a fourth embodiment of the present invention.

FIG. 23 is a flowchart illustrating an example of an operation flow before displaying the image of the abdominal cross-section according to the fourth embodiment. According to the present embodiment, as an example of the calculation of at least a portion of the abdominal outline, an outline of an approximate semi-circumference from the naval position is calculated. According to researches of the inventor, however, it was found that, even when the orientation information and motion information that are obtained do not satisfy the semi-circumference, based on information about the outline for 135 degrees (⅜ of the full circumference) from the naval point, the visceral fat area, the subcutaneous fat area, and the abdominal cross-sectional circumference may be estimated with almost the same accuracy. According to the present embodiment, as such, an example of processing will be described, assuming that obtainment of the information about the outline for at least 135 degrees (⅜ of the full circumference) allows a valid measurement.

At step S101, the user activates the measurement application 9Z for the measurement of the cross-sectional outline. After the measurement application 9Z is activated, the user inputs the actual measured value of the abdominal circumference preliminarily measured by the tape measure and the like to the smartphone 1 (step S111). Or, the actual measured value of the abdominal circumference may be retrieved from the user information preliminarily stored in the storage 9 of the smartphone 1. Note that the processing at step S111 does not need to be carried out before the start of the measurement but may be carried out after the end of the measurement at step S104. When the motion information is obtained by the acceleration sensor 16 at step S103, step S111 may be omitted.

Next, the measurement starts at step S102. According to the present embodiment, the naval position is set to the measurement start position. For example, the measurement starts when the side face 1C1 of the smartphone 1 is brought to meet the naval position. The user carries out the starting action preset to the smartphone 1 to start the measurement.

At step S103, the user moves the smartphone 1 along the A-A position on the surface of the abdomen 60. The user moves the smartphone 1 at a constant speed while maintaining its contact to the surface of the abdomen 60.

At step S103, the smartphone 1, under the pre-programed conditions, obtains the angular velocity (degree/second) as the orientation information by using the angular velocity sensor 18. The orientation information is obtained for a plurality of times according to the clock signal output from the timer 11. The orientation information obtained according to the clock signal is stored in the smartphone 1 together with the obtainment time information. This measurement is continually executed from the start at step S102 to the end at step S104. Note that the acceleration sensor 16 may measure the moving amount as the motion information. The motion information obtained by the acceleration sensor 16 is similar to that described in the first embodiment, and thus a description thereof will be omitted here.

Note that the control unit 10A, during execution of step S103, may generate sounds at predetermined intervals from the receiver 7 and the like of the smartphone 1. The user may move the smartphone 1 listening to the sound generated at predetermined intervals, which makes it easy for the user to move the smartphone 1 around the abdomen at a constant speed.

The user moves the smartphone 1 at a constant speed by at least the semi-circumference of the abdomen 60 while maintaining the contact of the smartphone 1 to the surface of the abdomen 60. According to the present embodiment, the semi-circumference refers to the motion from the naval to the center of the back. As described below, when the movement of the smartphone 1 is smaller than 135 degrees (3/8 of the full circumference), the accuracy in the calculation of the outline becomes insufficient, possibly causing an error in the characteristic coefficient of the outline. Accordingly, the smartphone 1 preferably notifies the user that data of 135 degrees (3/8 of the full circumference) or data of the semi-circumference are obtained.

When the smartphone 1 is move by at least the semi-circumference, the user carries out the ending action preset to the smartphone 1 to end the measurement (step S104). Alternatively, the control unit 10A may determine that the smartphone 1 has moved by the approximate semi-circumference when the orientation of the smartphone 1 has changed by 180 degrees from the start of the measurement and automatically end the measurement. When the smartphone 1 carries out such automatic recognition, the user does not need to carry out the ending action, and thereby the measurement is more simplified.

Or, when the user, based on the notification from the smartphone 1, knows that the data of 135 degrees (3/8 of the full circumference) have been obtained, the user may carry out the ending action and the like to end the measurement.

Note that when the control unit 10A, before the movement of the smartphone 1 reaches the semi-circumference, detects an error such as there is no change in the orientation information for a predetermined time or there is reverse of an increase or decrease in the orientation, the control unit 10A may automatically end the measurement.

When the measurement ends (step S104), the control unit 10A determines whether the information about at least the semi-circumference has been obtained (step S201). This determination may be made based on whether, as illustrated in FIG. 18, for example, the orientation information at the end of the measurement indicates at least 180 degrees. Or, the control unit 10A, based on the time when the measurement ends at step S104, may determine whether the data of at least the semi-circumference have been obtained.

At step S201, when it is determined that the information about at least the semi-circumference has been obtained, the control unit 10A, in a manner similar to the third embodiment, calculates the semi-circumference of the abdominal cross-sectional outline (step S115). The control unit 10A, by carrying out the integration of the angular velocity obtained at step S103 one time, calculates the orientation of the smartphone 1.

An example of the orientation information of the smartphone 1 when the information about at least the semi-circumference has been obtained is illustrated in FIG. 18 as described above. The control unit 10A, after calculating the semi-circumference of the abdominal cross-sectional outline at step S115, carries out correction processing (step S216) similar to that at step S116.

Note that the control unit 10A, as illustrated in FIG. 18, may use the orientation information and the motion information when the user carries out the starting action such as pressing a start button down and the like as the information at the start of the measurement (time: 0 second). Or, the orientation information and the motion information when the smartphone 1 has a predetermined posture may be used as the information at the start of the measurement (time: 0 second). That is, the time is set to 0 when the orientation sensor detects the predetermined posture in which the rear face 1B of the smartphone 1 held against the naval position, and data obtained thereafter may be used for calculation of the portion of the abdominal outline.

On the other hand, when at step S201 the control unit 10A determines that the obtained information does not satisfy the semi-circumference, the control unit 10A determines whether the obtained information satisfies 135 degrees (3/8 of the full circumference) (step S202). This determination may be made, for example, by determination whether the orientation information at the end of the measurement satisfies at least 135 degrees.

When at step S202 the control unit 10A determines that the obtained information satisfies at least 135 degrees (3/8 of the full circumference), the control unit 10A calculates the abdominal outline for 135 degrees (step S203). The control unit 10A, by carrying out the integration of the obtained angular velocity at step S103 one time, calculates the orientation of the smartphone 1.

Figure 24:
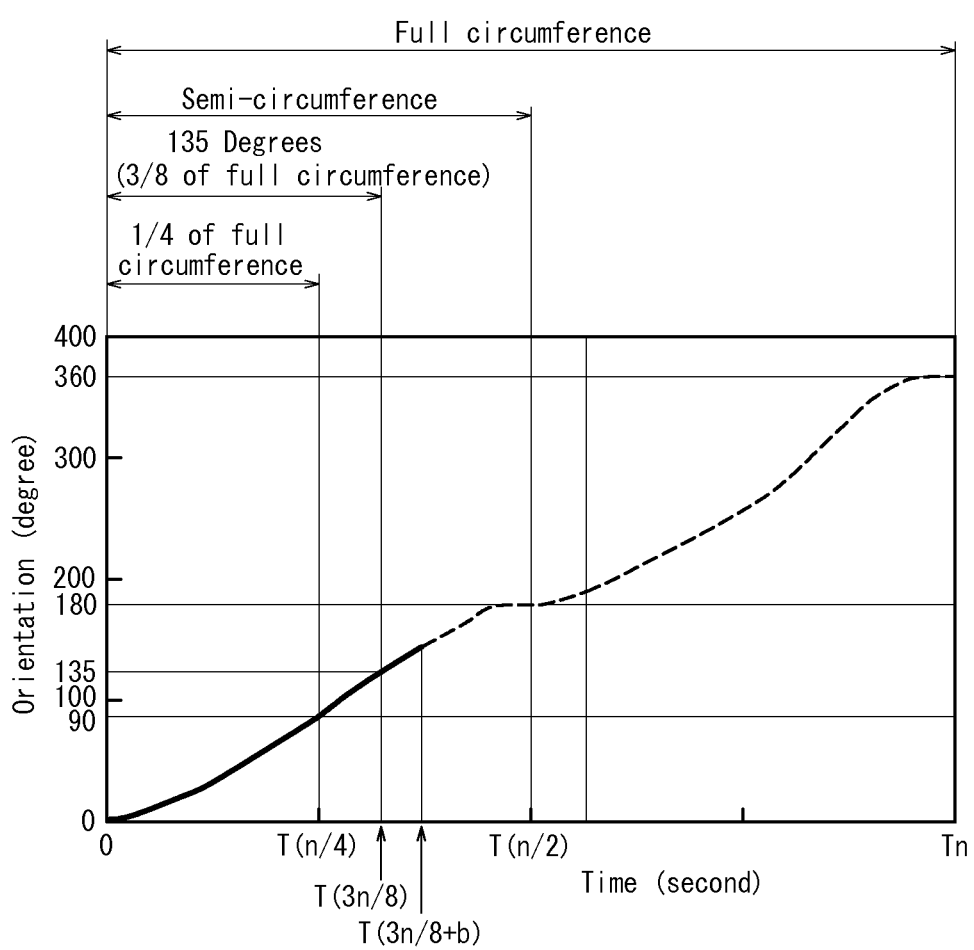
FIG. 24 is a diagram illustrating an example of orientation of the smartphone 1 according to the fourth embodiment of the present invention.

FIG. 24 illustrates an example of the orientation of the smartphone 1 according to the fourth embodiment. In FIG. 24, the horizontal axis indicates the measurement time, and the vertical axis indicates orientation information when the obtained information satisfies at least 135 degrees (3/8 of the full circumference) and less than the semi-circumference. With reference to FIG. 24, a method of extracting the information about the semi-circumference from the obtained orientation information will be described. The horizontal axis indicates the time; the measurement starts at 0 second and ends at T(3n/8+b) seconds. Here, n represents the full circumference, i.e., 360 degrees, and b represents an angle obtained by subtracting 135 degrees corresponding to 3/8 of the full circumference from the orientation at the end of the measurement. The vertical axis indicates the orientation of the smartphone 1. In the figure, a solid line represents the obtained information, and a dotted line represents a virtual line of unobtained information about a rest of the full circumference.

Figure 25:
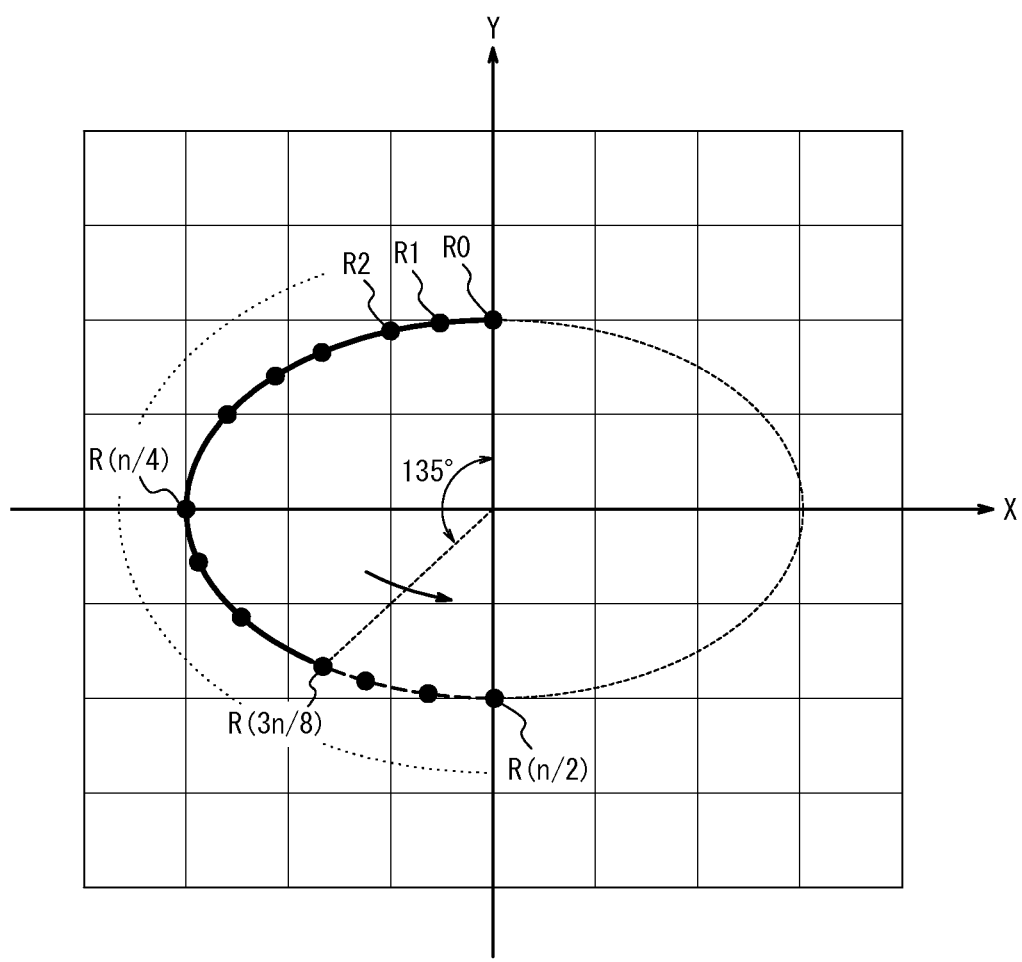
FIG. 25 is a diagram illustrating a cross-sectional outline calculated and corrected according to the fourth embodiment of the present invention.

At step S216, the smartphone 1 corrects the result of the calculation carried out at step S203. FIG. 25 is a diagram illustrating the cross-sectional outline corrected based on the orientation information and the motion information about the outline for 135 degrees (3/8 of the full circumference). In the figure, the record at time T(3n/8) and the record at T(n/2) are represented by R(3n/8) and R(n/2), respectively. In the figure, a solid bold line represents the calculated cross-sectional outline for 135 degrees (3/8 of the full circumference), and a dotted bold line represents an outline obtained by replicating the calculated cross-sectional outline between 90 degrees and 135 degrees. Note that the outline is considered to have a substantially oval shape, and a ratio of a long side to a short side is taken into account for the replication. A dotted narrow line in the figure represents an outline obtained by further replicating the outline between 0 degree and 180 degrees obtained by the above processing with respect to the Y-axis. In this way, replicating the outline between 90 degrees and 135 degrees allows obtainment of a curve of the outline smoothly connected from 0 degree to 180 degrees. Also, the inverting closed curve replicated with respect to the Y-axis may be obtained.

Here, a reason that, based on the orientation information and the motion information for 135 degrees (3/8 of the full circumference), the visceral fat area may be estimated with the same accuracy as that estimated based on the information about the semi-circumference will be described.

Figure 26:
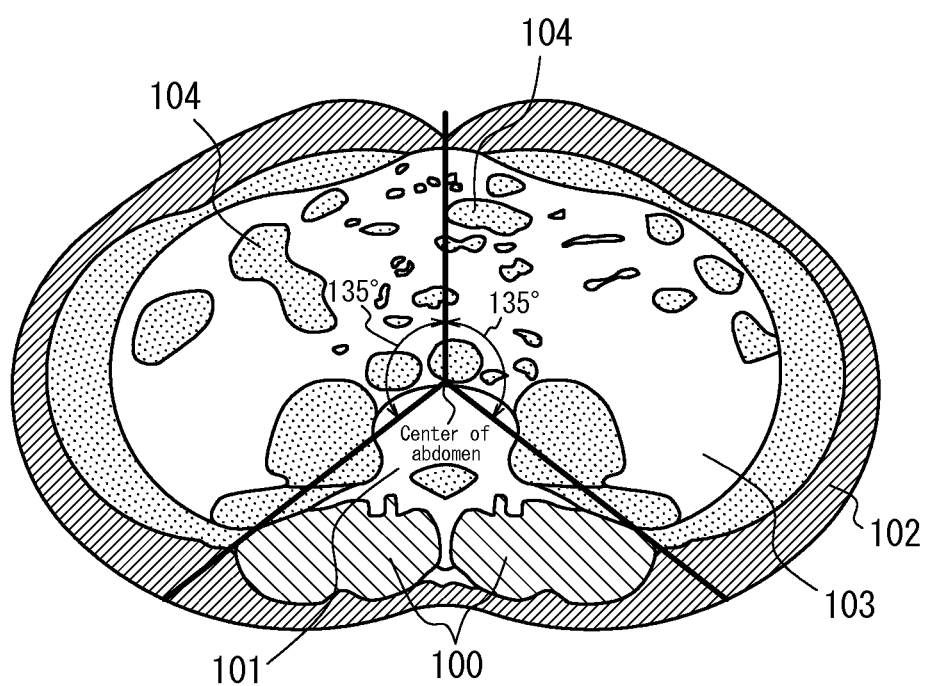
FIG. 26 is a diagram illustrating the abdominal cross-section.

FIG. 26 illustrates a cross-sectional view of the abdomen of an adult. FIG. 26 illustrates, in addition to erector spinae muscles 100 located on a dorsal side of the spinal column, a spine 101, a subcutaneous fat 102, a visceral fat 103, and an organ 104.

As can be seen from FIG. 26, the visceral fat 103 is present in a substantially concentrating manner in a region outside a straight line connecting the center of the abdomen and an outer side of the erector spinae muscles 100. Also, an angle formed between the straight line connecting the center of the abdomen and the outer side of the erector spinae muscles 100 and a straight line connecting the center of the abdomen and the naval (at top center in FIG. 26) is approximately 135 degrees as illustrated in FIG. 26. Therefore, according to the method of estimating the visceral fat from the characteristics of the shape of the abdominal outline employed by the present invention, the shape of the outline from 135 degrees to 180 degrees has a very small impact on a result of the estimation of the visceral fat area.

The smartphone 1, after the correction at step S216, extracts the characteristic coefficients from the curve of the cross-sectional outline for 135 degrees (3/8 of the full circumference) or the inverting closed curve (step S217). According to the present embodiment, in a manner similar to the third embodiment, the Fourier coefficients $Sa_1$, $Sa_2$, $Sa_3$, and $Sa_4$ those affect the visceral fat area are extracted as the characteristic coefficients of the visceral fat. Also, the Fourier coefficients $Sb_1$, $Sb_2$, $Sb_3$, and $Sb_4$ those affect the subcutaneous fat area are extracted as the characteristic coefficients of the subcutaneous fat. According to the present embodiment, further, Fourier series those affect the circumference of the abdominal cross-section are also extracted as the characteristic coefficient of the abdominal circumference.

The smartphone 1, by substituting the characteristic coefficients extracted at step S217 into the visceral fat area estimation equation, the subcutaneous fat area estimation equation, and the abdominal cross-sectional circumference estimation equation, estimates the user's visceral fat area A, subcutaneous fat area B, and abdominal cross-sectional circumference (step S218). Note that examples of the visceral fat area estimation equation and the subcutaneous fat area estimation equation correspond to aforementioned Formula 1 and Formula 2, respectively.

Next, the smartphone 1, based on the visceral fat area A and the subcutaneous fat area B estimated at step S218, selects an image having a highest similarity to the user's abdominal cross-section (step S119). Then, the smartphone 1, from the 25 types of images in the classification table of the images of the abdominal cross-section illustrated in FIG. 21, selects one image corresponding to the estimated user's visceral fat area A and subcutaneous fat area B. The selected image, similarly to the third embodiment, is displayed in the display 2A of the smartphone 1 (step S110).

Note that the processing from step S217 to step S110 is also carried out after calculation of the semi-circumference of the abdominal outline at step S115.

On the other hand, when it is determined at step S202 that the obtained information does not satisfy 135 degrees (3/8 of the full circumference), the control unit 10A ends the operation without displaying the image of the abdominal cross-section (step S204). Thereby, the smartphone 1 avoids confusing the user by displaying data having inadequate accuracy.

Although according to the present embodiment the motion information is obtained from the timer 11, the present invention is not limited thereto. For example, in a manner similar to the first embodiment, by using the acceleration sensor 16 as the second sensor unit and carrying out time integration of obtained acceleration information two times, the moving amount of the smartphone 1 may be calculated.

According to the present embodiment, as described above, even if the measured abdominal outline does not satisfy the semi-circumference, when the orientation information and the motion information for 135 degrees (3/8 of the full circumference) are obtained, the visceral fat area may be accurately estimated.

According to the present embodiment, also, in addition to the visceral fat area and the subcutaneous fat area, the abdominal cross-sectional circumference may also be estimated.

According to the present embodiment, also, during obtainment of the orientation information and the motion information, the smartphone 1 generates the sound at predetermined intervals. Thereby, the user may easily move the smartphone around the abdomen at a constant speed.

According to the present embodiment, also, when the measured abdominal outline does not satisfy 135 degrees (3/8 of the full circumference), the image of the abdominal cross-section is not displayed. Thereby, it is ensured that the smartphone 1 avoids confusing the user by displaying data having inadequate accuracy.

According to the present embodiment, further, the orientation information and the motion information after the smartphone 1 has the predetermined posture is used for calculation of a portion of the abdominal outline. Thereby, the smartphone 1 may always start the measurement while having a predetermined correct posture.

Figure 27A:
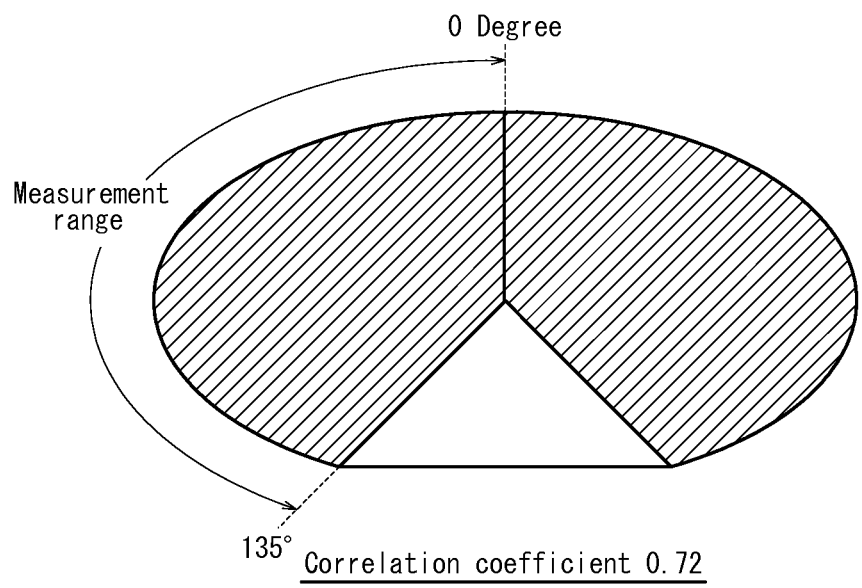
FIG. 27A is a diagram illustrating a comparison of complementing methods of the abdominal outline according to the fourth embodiment of the present invention.
Figure 27B:
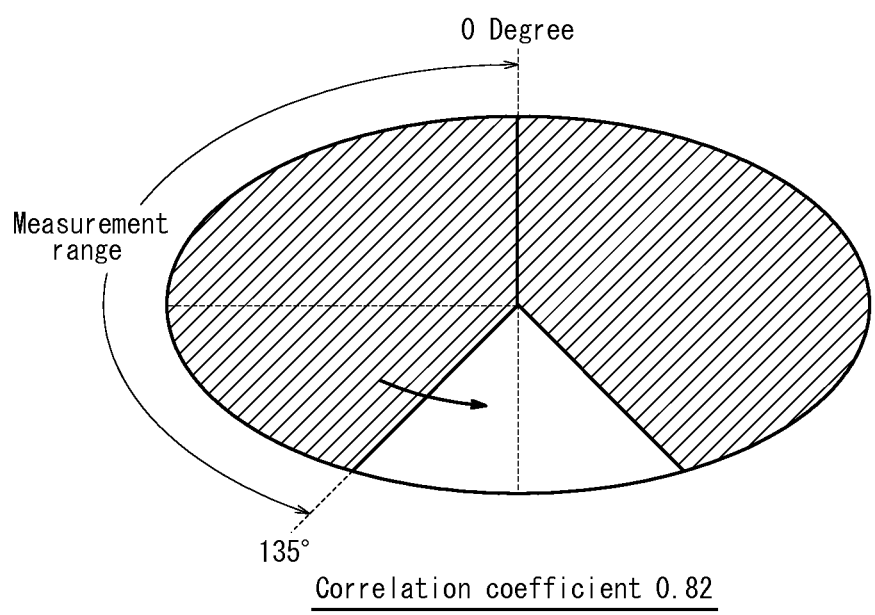
FIG. 27B is a diagram illustrating the comparison of complementing methods of the abdominal outline according to the fourth embodiment of the present invention.

Next, verification tests of the present embodiment were carried out, and thus an effect of the present invention was confirmed. For the measurement, a smartphone (model number: WX10K) manufactured by Kyocera Corporation was used. A correlation between the visceral fat area estimated from the obtained information and the visceral fat area obtained by the CT is evaluated by using correlation coefficients. As for the correction method of the abdominal outline, the method of complementing the outline from 135 degrees to 180 degrees with a straight line (FIG. 27A) and the method of complementing the outline from 135 degrees to 180 degrees by replicating an outline from 90 degrees to 135 degrees to serve as the data of the outline from 135 degrees to 180 degrees (FIG. 27B) were compared with each other. As a result, while the correlation coefficient obtained by the method of complementing the outline from 135 degrees to 180 degrees with the straight line was 0.72, the correlation coefficient obtained by the method of complementing the outline by replicating the data from 90 degrees to 135 degrees was 0.82, which is a better value. As can be seen from this result, as a method of complementing unmeasured data, the method of complementing the outline by replicating the data from 90 degrees to 135 degrees is more appropriate.

Table 1 shows, with respect to 105 male subjects, a correlation between the visceral fat area and the subcutaneous fat area estimated from the obtained information and the visceral fat area and the subcutaneous fat area obtained by the CT, categorized for each length of the measured abdominal outline.

TABLE 1

| Calculated circumferential outline | Correlation coefficient of visceral fat area (Male, n = 105, BMI <40) | Correlation coefficient of subcutaneous fat area (Male, n = 105, BMI <40) |
| --- | --- | --- |
| Full circumference | 0.81 | 0.90 or more |
| Semi-circumference | 0.82 | 0.90 or more |
| 135 degrees (⅜ of full circumference) | 0.82 | 0.90 or more |
| ¼ of full circumference | 0.78 | 0.90 or more |

As a result, when the outline of ¼ of the full circumference was calculated, the correlation coefficient of the visceral fat area is 0.78. On the other hand, when the outline for 135 degrees (⅜ of the full circumference) or more is calculated, the correlation coefficient of the visceral fat area is 0.82. Accordingly, it can be seen that the calculation of the outline for 135 degrees (⅜ of the full circumference) as described above allows the estimation of the visceral fat area having an adequate accuracy. It can be also seen that the subcutaneous fat area of the outline of at least ¼ of the full circumference does not rely on the calculated outline but allows obtainment of a high correlation coefficient of at least 0.90.

Table 2 shows a result of the estimation of the abdominal cross-sectional circumference according to the present embodiment. That is, Table 2 shows, with respect to each of the calculated circumferential outline, correlation coefficients between the result of the estimation of the abdominal circumference from a portion of the outline and an actual measured abdominal circumference. Shown at right end of Table 2 are, as reference data, correlation coefficients between a result of the calculation of the abdominal circumference by multiplying the calculated circumference of the portion of the outline by a predetermined multiple and the actual measured abdominal circumference. The calculated circumference of the portion of the outline refers to the moving amount of the smartphone 1 calculated from the obtained motion information.

TABLE 2

| Calculated circumferential outline | Estimation from partial outline shape (Male, n = 105, BMI <40) | Multiplying partial outline by prescribed multiple (Male, n = 105, BMI <40) |
| --- | --- | --- |
| Semi-circumference | 0.90 | 0.99 (double of ½ of full circumferential outline) |
| 135 degrees (⅜ of full circumference) | 0.85 | 0.79 (⁸⁄₃ times of ⅜ of full circumferential outline) |
| ¼ of full circumference | 0.83 | 0.74 (four times of ¼ of full circumferential outline) |

As can be seen from Table 2, as for the semi-circumference outline, doubling the calculated portion of the outline has a higher correlation coefficient: 0.99. On the other hand, as for the calculated outline for 135 degrees (⅜ of the full circumference) or ¼ of the full circumference, the circumference estimated from the portion of the outline has a higher correlation coefficient. Since the abdominal shape is bilaterally symmetric, when the circumference of a left half outline or a right half outline may be measured, the abdominal circumference obtained by simply doubling the circumference of the left half outline or the right half outline has a higher accuracy. On the other hand, when the measured outline does not satisfy the semi-circumference, it is considered that the full circumference of the abdomen estimated from the shape of the outline has a higher accuracy.

Note that the present invention is not limited to the above embodiments but may be modified or changed in a variety of manners. For example, the calculation and the estimation may be carried out by using either one of the visceral fat area and the subcutaneous fat area. Also, the classification of the image of the abdominal cross-section does not need to be based on the combination of the visceral fat area and the subcutaneous fat area but may be based on either one of them.

Next, a system according to the embodiment of the present invention will be described in detail with reference to the drawing.

Figure 28:
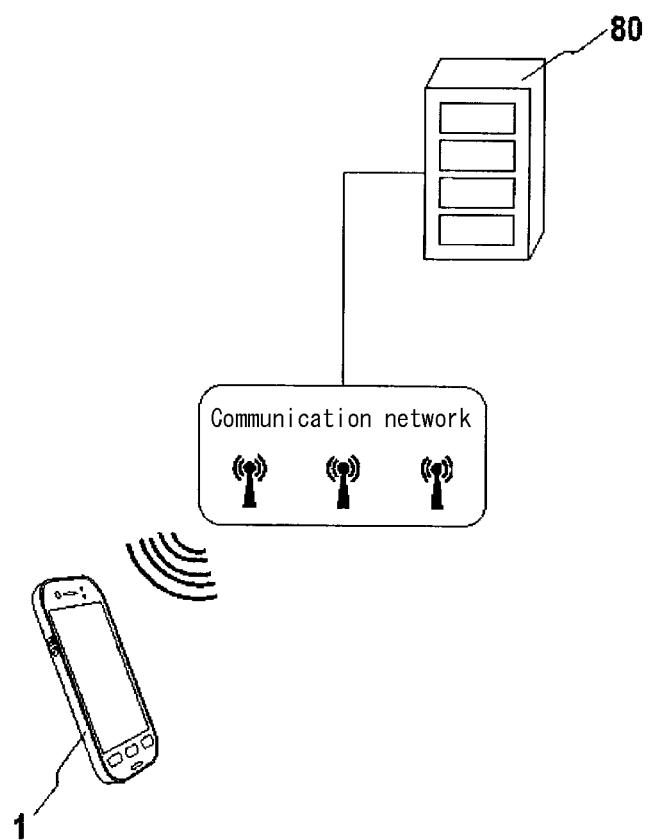
FIG. 28 is a conceptual diagram illustrating an apparatus having a communication means and a system according to the embodiments of the present invention.

A system according to the embodiment illustrated in FIG. 28 includes a server 80, the smartphone 1, and a communication network. As illustrated in FIG. 28, the result of the calculation of the cross-sectional outline measured by the smartphone 1 is transmitted, via the communication network, to the server 80 which classifies and determines the cross-sectional outline and sends an image and advice to the user. The smartphone 1 may display, in the display 2A, the image and the like transmitted from the server 80. Since the use of a communication means of the smartphone 1 allows the server 80 to collect information from a plurality of users, an accuracy in the classification and determination is improved. Alternatively, the orientation information, the motion information, and the abdominal circumference those are obtained may be transmitted to the server 80. In this case, the server 80 calculates the cross-sectional outline, thereby reducing a load on the controller 10 of the smartphone 1 used by the user to carry out the calculation and thus allowing size reduction and simplification of the smartphone 1. Also, the calculation speed is increased.

Although in the system according to the present embodiment the smartphone 1 and the server 80 are connected via the communication network, the system of the present invention is not limited thereto. The system only needs a probe for moving along the surface of the object, a first sensor unit for obtaining the orientation information of the probe, a device unit for obtaining motion information of the probe, and a control unit for calculating the cross-sectional outline of the object. Also, each of these components may be connected via a communication means.

For a full and clear disclosure of the present invention, characteristic embodiments are described above. However, claims attached hereto are not limited to the above embodiments but should be configured so as to embody all modifications and possible alternates those skilled in the art may create within the fundamentals set forth herein.

For example, although in the above embodiments the smartphone 1 is used as the apparatus, the apparatus of the present invention is not limited thereto but only needs to include the first sensor unit, the device unit, and the control unit. Further, the apparatus of the present invention does not need to include the first sensor unit, the device unit, and the control unit therein but those units may be independent of one another.

Also, although in the above embodiments the measurement of the abdominal cross-sectional outline is described, the present invention is applicable also to measurements of cross-sectional outlines of other structures.

Also, although in the above embodiments the orientation sensor and the angular velocity sensor are used as the first sensor unit, the first sensor unit may be constituted by using a different item such as, for example, the inclination sensor and the like, as long as being capable of obtaining the orientation information of the apparatus thereof.

Also, although in the above embodiments the acceleration sensor or the electronic tape measure is used as the second sensor unit, the second sensor unit may be constituted by using a different item such as, for example, an electronic roller telemeter for obtaining the motion information by detecting the number of rotations of a wheel, as long as being capable of obtaining the motion information of the apparatus thereof.

Further, although in the above embodiments examples of the measurements of the cross-sectional outline of the full circumference, the semi-circumference, or ¼ of the full circumference of the object are described, other amounts may also be measured. For example, measuring a cross-sectional outline of two circuits of the subject and averaging thus obtained data allows highly accurate measurement with less fluctuation.

Many aspects of the present disclosure are shown as a series of operations executed by hardware such as a computer system and the like that are capable of executing program instructions. The hardware such as the computer system and the like include, for example, a general-purpose computer, a PC (personal computer), a special purpose computer, a workstation, a PCS (Personal Communications System: a personal mobile communication system), a mobile (cellular) phone, a mobile phone with a data processing function, an RFID receiver, a gaming machine, an electronic notepad, a laptop computer, a GPS (Global Positioning System) receiver, and a programmable data processing apparatus. Note that in each of the embodiments various operations are executed by a dedicated circuit (for example, individual logic gates interconnected for execution of a particular function) implemented by a program instruction (software), or a logic block, a program module and the like those are executed by at least one processor. Such at least one processor for executing the logical block, the program module and the like includes, for example, at least one microprocessor, CPU (Central Processing Unit), ASIC (Application Specific Integrated Circuit), DSP (Digital Signal Processor), PLD (Programmable Logic Device), FPGA (Field Programmable Gate Array), a processor, a controller, a microprocessor, an electronic apparatus, and other apparatuses designed to be able to execute the functions described herein and/or any combination of these apparatuses. The embodiments described herein are implemented by, for example, hardware, software, firmware, middleware, a microcode, or any combination thereof. The instruction may be a program code or a code segment for executing a necessary task. Also, the instruction may be stored in a machine-readable non-transitory storage medium or other media. The code segment may indicate a procedure, a function, a subprogram, a program, a routine, a subroutine, a module, a software package, a class or an instruction, a data structure or a program statement, or any combination thereof. The code segment transmits and/or receives information, data parameters, variables or stored contents with another code segment or a hardware circuit, thereby connecting with the another code segment or the hardware circuit.

The network used herein includes, unless otherwise specified, Internet, an ad-hoc network, LAN (Local Area Network), WAN (Wide Area Network), MAN (Metropolitan Area Network), a cellular network, WWAN (Wireless Wide Area Network), WPAN (Wireless Personal Area Network), PSTN (Public Switched Telephone Network), a terrestrial wireless network (Terrestrial Wireless Network), other networks, and any combination thereof. Components of the wireless network include, for example, an access point (e.g., a Wi-Fi access point), a femtocell and the like. Further, a wireless communication apparatus may be connected with the wireless network employing Wi-Fi, Bluetooth (registered trademark), a cellular communication technology (e.g., CDMA (Code Division Multiple Access), TDMA (Time Division Multiple Access), FDMA (Frequency Division Multiple Access), OFDMA (Orthogonal Frequency Division Multiple Access), SC-FDM (Single-Carrier Frequency Division Multiple Access)), or other wireless technologies and/or wireless technical standards. The network may employ one or more technologies such as, for example, UTMS (Universal Mobile Telecommunications System), LTE (Long Term Evolution), EV-DO (Evolution-Data Optimized or Evolution-Data Only), GSM (registered trademark) (Global System for Mobile communications), WiMAX (Worldwide Interoperability for Microwave Access), CDMA-2000 (Code Division Multiple Access-2000), and TD-SCDMA (Time Division Synchronous Code Division Multiple Access).

A configuration of a circuit such as the communication unit provides functionality by using a variety of wireless communication networks such as, for example, WWAN, WLAN, WPAN and the like. WWAN may be a CDMA network, a TDMA network, an FDMA network, an OFDMA network, an SC-FDMA network and the like. The CDMA network may be implemented with one or more RAT (Radio Access Technology) such as CDMA-2000, Wideband-CDMA (W-CDMA) and the like. CDMA-2000 includes standards of IS-95, IS-2000, and IS-856. The TDMA network may be implemented with the RAT such as GSM (registered trademark), D-AMPS (Digital Advanced Phone System) and the like. GSM (registered trademark) and W-CDMA are described in documents issued by a consortium called 3rd Generation Partnership Project (3GPP). CDMA-2000 is described in documents issued by a consortium called 3rd Generation Partnership Project 2 (3GPP2). WLAN may be a network of IEEE802.11x. WPAN may be a Bluetooth (registered trademark) network, or a network of IEEE802.5x or another. CDMA may be implemented as the wireless technology such as UTRA (Universal Terrestrial Radio Access) or CDMA-2000. TDMA may be implemented by the wireless technologies such as GSM (registered trademark)/GPRS (General Packet Radio Service)/ EDGE (Enhanced Data Rates for GSM (registered trademark) Evolution). OFDMA may be implemented by the wireless technologies such as IEEE (Institute of Electrical and Electronics Engineers) 802.11 (Wi-Fi), IEEE802.16 (WiMAX), IEEE802.20, E-UTRA (Evolved UTRA) and the like. These technologies may be used for any combination of WWAN, WLAN and/or WPAN. Also, these technologies may be implemented to use a UMB (Ultra Mobile Broadband) network, a HRPD (High Rate Packet Data) network, a CDMA20001X network, GSM (registered trademark), LTE (Long-Term Evolution) and the like.

The storage used herein may further serve as a computer-readable tangible carrier (medium) that falls under categories of a solid state memory, a magnetic disc, and an optical disc. Such a medium stores an appropriate set of computer instructions such as program modules for making a processor to execute the techniques disclosed herein, and a data structure. The computer-readable medium includes an electrical connection with one or more cables, a magnetic disc storage medium, a magnetic cassette, a magnetic tape, other magnetic and optical storage apparatuses (for example, CD (Compact Disk), a laser disc (registered trademark), DVD (registered trademark) (Digital Versatile Disc), a floppy (registered trademark) disk, and Blu-ray disk (registered trademark)), a mobile computer disc, RAM (Random Access Memory), ROM (Read-Only Memory), EPROM, EEPROM, a rewritable and programmable ROM such as a flash memory, other tangible storage media capable of storing information, and any combination thereof. The memory may be provided inside and/or outside a processor/processing unit. As used herein, the term "memory" refers to all types of memories including a long term storage, a short-term storage, a volatile storage, a nonvolatile storage, and other storages, and is not limited to a particular type, a particular number of the memories, or a type of the memory to store information.

Note that the system having various modules and/or units for executing particular functions is disclosed herein, and those modules and/or units are schematically illustrated for a simple description of functionalities thereof and thus do not represent particular hardware/software. In this sense, those modules, units, and other components may be hardware and/or software implemented for substantially executing the particular functions described herein. Variety of functions of different components may be executed by any combination of hardware and/or software or separated hardware and/or software and thus these components may be used separately, or in any combination thereof. Also, an input/output or I/O device or a user interface including, but not limited to, a keyboard, a display, a touchscreen, a pointing device and the like may be connected to the system directly or via an intervening I/O controller. As described above, various aspects of the present disclosure may be implemented in various different manners, and thus all of those manners are included in the scope of the present disclosure.

REFERENCE SIGNS LIST 1 smartphone
1A front face
1B rear face
1C1 to 4, 71C2 side face
2, 72 touchscreen display
2A display
2B touchscreen
3 button
4 illuminance sensor
5 proximity sensor
6 communication unit
7 receiver
8 microphone
9 storage
9A control program
9B message application
9C browser application
9Z measurement application
10 controller
10A control unit
11 timer
12, 13 camera
14 connector
15 motion sensor
16 acceleration sensor
17 orientation sensor
18 angular velocity sensor
19 inclination sensor
20, 70 housing
60 abdomen
71 electronic tape measure
73 tape measure
74 stopper
80 server
100 elector spinae muscles
101 spine
102 subcutaneous fat
103 visceral fat
104 organ

The invention claimed is:

1. A method of estimating body fat with an apparatus comprising a control unit, the method comprising:
    a step of obtaining orientation information by a first sensor and motion information of the apparatus itself by a device;
    a step of calculating a portion of an abdominal outline by the control unit, based on the orientation information and the motion information;
    a step of calculating shape characteristics by the control unit, based on the calculated portion of the abdominal outline; and
    a step of estimating by the control unit, based on the shape characteristics, at least one of a visceral fat area and a subcutaneous fat area of an abdominal cross-section,
    wherein the step of calculating the shape characteristics is performed by extracting characteristic coefficients based on the portion of the abdominal outline.

2. The method of estimating body fat according to claim 1, further comprising a step of controlling a display by the control unit to display an image of the abdominal cross-section corresponding to at least one of the visceral fat area and the subcutaneous fat area that are estimated.

3. The method of estimating body fat according to claim 1, further comprising a step of carrying out correction by the control unit such that the abdominal outline forms a continuous closed curve, based on the portion of the abdominal outline.

4. The method of estimating body fat according to claim 1, further comprising a step of estimating, when the portion of the abdominal outline is shorter than a predetermined portion of the abdominal outline, based on a portion of the abdominal outline that is shorter than the predetermined portion of the abdominal outline and suitable for the estimation, at least one of a visceral fat area and a subcutaneous fat area of the abdominal cross-section.

5. The method of estimating body fat according to claim 1, wherein the calculated abdominal outline is less than the semi-circumference.

6. A method of estimating body fat with an apparatus comprising a control unit, the method comprising:
   a step of obtaining orientation information by a first sensor and motion information of the apparatus itself by a device;
   a step of calculating a portion of an abdominal outline by the control unit, based on the orientation information and the motion information;
   a step of calculating shape characteristics by the control unit, based on the calculated portion of the abdominal outline; and
   a step of estimating by the control unit, based on the shape characteristics, a circumference of an abdominal cross-section,
   wherein the step of calculating the shape characteristics is performed by extracting characteristic coefficients based on the portion of the abdominal outline.

7. The method of estimating body fat according to claim 6, wherein the calculated abdominal outline is less than the semi-circumference.

8. An apparatus comprising:
   a control unit;
   a first sensor communicatively coupled with the control unit, the first sensor configured to obtain orientation information of the apparatus itself;
   a device communicatively coupled with the control unit, the device configured to obtain motion information of the apparatus itself; and
   a display configured to display an image of an abdominal cross-section corresponding to at least one of a visceral fat area and a subcutaneous fat area of the abdominal cross-section estimated based on shape characteristics calculated based on a portion of an abdominal outline calculated based on the orientation information and the motion information,
   wherein the calculation of the shape characteristics is performed by extracting characteristic coefficients based on the portion of the abdominal outline.

9. The apparatus according to claim 8, wherein the first sensor includes an orientation sensor, an angular velocity sensor, or an inclination sensor.

10. The apparatus according to claim 8, wherein the device includes a second sensor communicatively coupled with the control unit, the second sensor configured to obtain the motion information of the apparatus itself.

11. The apparatus according to claim 10, wherein the second sensor includes an acceleration sensor or an electronic tape measure.

12. The apparatus according to claim 8, wherein the device includes a timer.

13. The apparatus according to claim 8, wherein the apparatus further includes a sound generation unit communicatively coupled with the control unit, the sound generation unit configured to generate sound at predetermined intervals while the device is obtaining the motion information.

14. The apparatus according to claim 8, wherein the control unit is configured to operate the display, and
   wherein, when a predetermined range of the orientation information is not obtained, the display is prevented from displaying the image of the abdominal cross-section by the control unit.

15. The apparatus according to claim 8, further wherein the control unit, by using the orientation information and the motion information obtained after the apparatus has a predetermined posture ready for a measurement, calculates the portion of the abdominal outline.

16. The apparatus according to claim 8, wherein the calculated abdominal outline is less than the semi-circumference.

17. A system comprising:
   a probe;
   a first sensor configured to obtain orientation information of the probe;
   a device configured to obtain motion information of the probe; and
   a control unit communicatively coupled with the first sensor and the device, the control unit configured to estimate, based on shape characteristics calculated based on a portion of an abdominal cross-section calculated based on the orientation information and the motion information, at least one of a visceral fat area and a subcutaneous fat area of the abdominal cross-section,
   wherein the calculation of the shape characteristics is performed by extracting characteristic coefficients based on the portion of the abdominal outline.

18. The system according to claim 17, wherein the calculated abdominal outline is less than the semi-circumference.

* * * * *